United States Patent
Kishimoto et al.

(10) Patent No.: US 8,075,493 B2
(45) Date of Patent: Dec. 13, 2011

(54) BLOOD PRESSURE MEASURING DEVICE

(75) Inventors: Hiroshi Kishimoto, Kyoto (JP); Masayuki Fukutsuka, Uji (JP)

(73) Assignee: OMRON Healthcare Co., Ltd., Kyoto-shi (JP)

( * ) Notice: Subject to any disclaimer, the term of this patent is extended or adjusted under 35 U.S.C. 154(b) by 1373 days.

(21) Appl. No.: 11/651,545

(22) Filed: Jan. 10, 2007

(65) Prior Publication Data
US 2007/0197923 A1 Aug. 23, 2007

(30) Foreign Application Priority Data

Jan. 13, 2006 (JP) ................................ 2006-006496

(51) Int. Cl.
*A61B 5/02* (2006.01)
*A62C 35/00* (2006.01)
(52) U.S. Cl. ............... 600/499; 137/355.16; 137/355.26
(58) Field of Classification Search .................... 600/499
See application file for complete search history.

(56) References Cited

U.S. PATENT DOCUMENTS

| | | | |
|---|---|---|---|
| 2,629,630 A * | 2/1953 | Roark | 137/355.17 |
| 3,621,845 A * | 11/1971 | Oates | 600/490 |
| 3,762,411 A | 10/1973 | Lloyd et al. | |
| 3,777,840 A | 12/1973 | Botnick et al. | |
| 4,417,703 A | 11/1983 | Weinhold | |
| 4,768,546 A | 9/1988 | Brusadin et al. | |
| 5,236,143 A | 8/1993 | Dragon | |
| 6,068,601 A | 5/2000 | Miyazaki et al. | |
| 6,199,784 B1 | 3/2001 | Wang et al. | |
| 6,322,517 B1 | 11/2001 | Yamamoto et al. | |
| 6,344,025 B1 | 2/2002 | Inagaki et al. | |
| 6,616,080 B1 | 9/2003 | Edwards et al. | |
| 6,731,956 B2 | 5/2004 | Hanna et al. | |
| 6,799,808 B1 | 10/2004 | Walters | |
| 2002/0095091 A1 | 7/2002 | Che et al. | |
| 2003/0146332 A1 | 8/2003 | Vinding | |
| 2004/0010198 A1 | 1/2004 | Yamakoshi et al. | |
| 2005/0234350 A1 | 10/2005 | Sawanoi et al. | |

(Continued)

FOREIGN PATENT DOCUMENTS

DE 101 28 337 1/2003

(Continued)

OTHER PUBLICATIONS

European Office Action dated May 22, 2007, directed to EP Patent Application No. 06016579.2, Partial European Search Report; 7 pages.

(Continued)

*Primary Examiner* — Miranda Le
*Assistant Examiner* — Meredith Weare
(74) *Attorney, Agent, or Firm* — Morrison & Foerster LLP

(57) ABSTRACT

A winding unit for an air tube provided to a blood pressure monitor includes a reel body rotatably supported by a case body, and a helical spring that biases the reel body in the direction in which the air tube is wound. The air tube includes a wound portion wound by the reel body, a fixed portion immovably fixed to the case body, and a freely movable portion that freely moves as the reel body rotates. The reel body has a housing containing the freely movable portion. A second free-movement end is disposed at an eccentric position relative to a rotational center of the reel body. The winding unit is thus configured to prevent bending of the air tube in the winding unit and to be downsized.

5 Claims, 20 Drawing Sheets

U.S. PATENT DOCUMENTS

| | | |
|---|---|---|
| 2005/0240109 A1 | 10/2005 | Inoue et al. |
| 2006/0058689 A1 | 3/2006 | Kishimoto et al. |
| 2007/0038133 A1 | 2/2007 | Kishimoto et al. |

FOREIGN PATENT DOCUMENTS

| | | | |
|---|---|---|---|
| EP | 1 048 266 | | 11/2000 |
| EP | 1048266 A1 | * | 11/2000 |
| EP | 1 125 551 | | 8/2001 |
| EP | 1 394 094 | | 3/2004 |
| EP | 1 547 517 | | 6/2005 |
| EP | 1 752 090 A2 | | 2/2007 |
| GB | 2 114 096 A | | 8/1983 |
| JP | 62-130606 | | 8/1987 |
| JP | 63-106280 | | 5/1988 |
| JP | 64-019403 | | 1/1989 |
| JP | 3-97443 | | 4/1991 |
| JP | 4-34803 | | 8/1992 |
| JP | 05-085673 | | 4/1993 |
| JP | 10-295654 | | 11/1998 |
| JP | 2000-83912 | | 3/2000 |
| RU | 2 190 345 | | 10/2002 |
| RU | 2231967 | | 11/2003 |
| TW | 336163 | | 7/1998 |
| WO | WO 00/31847 | | 6/2000 |
| WO | WO 01/73911 A1 | | 10/2001 |

OTHER PUBLICATIONS

Russian Official Action mailed on Jun. 28, 2007, directed to Russian Patent Application No. 2006129230/14; 7 pages.

Extended European Search Report mailed on Jul. 26, 2007, directed to EP Patent Application No. 06016579.2; 16 pages.

Russian Office Action dated Dec. 18, 2007, directed to Russian Patent Application No. 2006129230/14; 18 pages.

Kishimoto, H. et al., U.S. Office Action mailed on Feb. 4, 2009, directed to U.S. Appl. No. 11/502,394; 19 pages.

Kishimoto, H. et al., U.S. Office Action mailed on Sep. 8, 2009, directed to U.S. Appl. No. 11/502,394; 20 pages.

Russian Action directed at counterpart foreign application RU 2007101333 mailed on Jun. 6, 2008; 12 pages.

European Search Report dated Apr. 13, 2007, directed at counterpart EP application No. 07000247.

Japanese Notice of Grounds of Rejection mailed May 24, 2011, directed towards counterpart patent application No. JP2006-006496; 4 pages.

* cited by examiner

BLOOD PRESSURE MEASURING DEVICE

BACKGROUND OF THE INVENTION

1. Field of the Invention

The present invention relates to a blood pressure measuring device (hereinafter also referred to simply as blood pressure monitor) configured to have a cuff and a main-unit casing connected by a flexible connection tube and to allow the connection tube to be wound by a winding device provided within the main-unit casing.

2. Description of the Background Art

Recently, for early detection of lifestyle-related diseases whose main cause is hypertension or for blood pressure management, blood pressure monitors that can be used at home have become widespread. Usually, to measure a blood pressure value, a cuff including a fluid bag for pressing an artery located within a living body is wrapped around the body surface of the living body, and arterial pressure pulse waves caused in the artery by inflation and deflation of the wrapped fluid bag are detected to measure the blood pressure value.

Here, the cuff refers to a band-shaped structure that has a bladder and that can be wrapped around a part of a living body, for use in measurement of arterial pressure of an upper limb/lower limb by supplying such a fluid as gas or liquid into the bladder. Thus, the cuff is a term representing the concept including the fluid bag as well as a wrapping member for wrapping the fluid bag around a part of the living body, and the cuff is also called arm band or manchette depending on the case.

For the so-called upper-arm blood pressure monitor using an upper arm as a site for taking a measurement, the structure is employed that connects, by an air tube which is a flexible connection tube, a main-unit casing in which for example a pump and a valve are provided that are components of an inflation/deflation mechanism for inflating/deflating an air bag serving as the fluid bag, and a cuff containing the air bag. Therefore, preferably the upper-arm blood pressure monitor is superior in terms of housing of the cuff, air tube and main-unit casing while the monitor is not in use, and it is required that the components can be housed compactly and that the operation of housing the components is easy.

As examples of the upper-arm blood pressure monitor improved in terms of housing property, those disclosed in Japanese Utility-Model Laying Open No. 64-019403 and Japanese Utility-Model Laying-Open No. 62-130606 for example are known. However, any of the disclosed monitors merely has, in a main-unit casing, a cuff housing for housing a cuff. Regarding the air tube, it is merely intended that the air tube is folded to be housed in an air-tube housing that is provided in parallel with the cuff housing or the folded air tube is inserted into and held in a hollow portion of a tubular cuff.

As for the blood pressure monitor configured in the manner as described above, a user is entirely responsible for the operation of housing the air tube. If the user handles the air tube carelessly, the air tube could be bent, twisted or caught between the main-unit casing and the open/close cover. In such a case, at the worst, the air tube could be broken.

SUMMARY OF THE INVENTION

In view of the above-described problems and with the purpose of improving the property of housing the air tube and ease of handling the air tube, the inventors of the present invention conceived the idea of configuring a blood pressure monitor to have a winding unit within the main-unit casing and use the winding unit to retract the air tube, which has been drawn out from the main-unit casing, into the main-unit casing. With this configuration, the air tube is easily and surely housed within the main-unit casing by means of the winding unit and the possibility of damage to the air tube is eliminated.

In those fields other than the field of the blood pressure monitor, various winding devices used for winding up a long tube have been invented (see for example Japanese Patent Laying-Open No. 63-106280). For the winding device winding up a long tube, it is necessary to have an anti-twist mechanism for preventing twisting of the long tube which is wound up. Japanese Patent Laying-Open No. 05-085673 is a document disclosing a winding device provided with this anti-twist mechanism.

The winding device disclosed in Japanese Patent Laying-Open No. 05-085673 is configured to have a chamber that is provided within a rotary drum around which such a long member as hose is wound and that houses a part of the long member. Further, the part of the long member that is housed within the chamber is configured to have at least a predetermined length so that the part is freely movable as the rotary drum rotates. The two ends of the freely movable part of the long member are fixed respectively to the peripheral wall of the rotary drum and a support portion supporting the rotary drum, thereby preventing the long member from twisting.

However, if the winding device having the anti-twist mechanism disclosed in Japanese Patent Laying-Open No. 05-085673 is housed in a main-unit casing of a blood pressure monitor, the following problems arise.

In terms of ease of handling by a user, it is necessary that a part of the air tube that can be drawn out from the main-unit casing has at least a predetermined length. For meeting this condition, it is necessary to increase the number of turns of the air tube wound around a reel body (rotary drum) of the winding unit, or increase the outer dimension of the reel body around which the air tube is wound and thereby increase the length per turn of the air tube wound around the outer peripheral surface of the reel body.

However, in order to speedily supply and discharge air into and out of an air bag by means of an inflation/deflation mechanism, the inner diameter of the air tube has to be increased. Further, in order for the air tube to have strength that is enough to endure repeated use, the wall of the air tube has to be thickened. As a result, it is inevitable that the air tube is a flexible tube having a certain thickness. Therefore, in the case where the number of turns of the air tube wound around the reel body is increased or the length per turn of the air tube wound around the outer peripheral surface of the reel body is increased, the winding unit is also increased in size, resulting in inevitable increase in size of the main-unit casing itself of the blood pressure monitor.

In order to downsize the winding unit for avoiding increase in size of the main-unit casing of the blood pressure monitor, it is the only solution to downsize the housing (chamber) that is provided within the reel body of the winding unit to house the freely-movable part of the air tube. However, if this configuration is employed, there arises a problem that the air tube is bent. FIGS. 20 to 22 are each a schematic cross-sectional view of a winding unit, used for illustrating this problem.

As shown in FIG. 20, the winding unit is configured to draw an air tube, from a rotational center O of a reel body 153 housed within a case body, in the direction of the rotational axis of reel body 153, to wind up a portion to be wound (wound portion) 162 of the drawn air tube around an outer peripheral surface 153b of reel body 153, and to allow wound portion 162 of the air tube to be drawn out of the case body from a draw-out opening 156 provided at a predetermined position of the case body. In order to prevent the air tube from twisting due to rotation of reel body 153, it is necessary to configure the winding unit to provide the air tube with a freely movable portion 164 that freely moves as reel body 153 rotates, to house freely movable portion 164 of the air tube in a housing 153a provided within reel body 153, and to fix, to reel body 153, a free-movement end 165 located at the boundary between wound portion 162 and freely movable portion 164 of the air tube. In order to allow freely movable portion 164 of the air tube that is housed in housing 153a to move freely within housing 153a, freely movable portion 164 of the air tube has to be extended to detour within housing 153a. Further, in order to have a predetermined length or longer of the part, which can be drawn out from the main-unit casing, of the air tube, it is necessary that freely movable portion 164 of the air tube, which is disposed to detour within housing 153a so that it is freely movable within housing 153a, has to be made long according to the length of the air-tube part that can be drawn out. In this case, as shown in the drawing, freely movable portion 164 of the air tube is housed in the greatly curved state within housing 153a of reel body 153.

With the winding unit thus configured, as the air tube is drawn out in the direction of an arrow B shown in FIGS. 21 and 22, reel body 153 is rotated in the direction of an arrow C shown in FIGS. 21 and 22 and accordingly wound portion 162 of the air tube is continuously fed out from draw-out opening 156. At this time, freely movable portion 164 of the air tube moves within housing 153a in reel body 153 while curved portions 164a, 164b of freely movable portion 164 also move within housing 153a according to movement of free-movement end 165 that is a position where freely movable portion 164 is fixed to reel body 153. As freely movable portion 164 moves, if housing 153a does not have an adequate size, freely movable portion 164 bends as shown in FIGS. 21 and 22. The bending of the air tube considerably interrupts flow of air. In addition, after repeated use, the bending of the air tube causes the air tube to be broken at the bent portion of the air tube.

An object of the present invention is to provide a blood pressure measuring device having a winding unit that can be made compact while preventing bending of a freely movable air-tube portion within a housing provided inside a reel body.

According to the present invention, a blood pressure measuring device includes: a cuff having an inflatable/deflatable fluid bag; a main-unit casing in which an inflation/deflation mechanism inflating/deflating the fluid bag is disposed; a flexible connection tube connecting the fluid bag and the inflation/deflation mechanism; and a winding unit capable of retracting the connection tube that is drawn out from the main-unit casing into the main-unit casing. The winding unit includes a case body immovably fixed to the main-unit casing, a reel body rotatably supported by the case body, and an elasticity application portion applying elasticity to the reel body in a direction in which the connection tube is wound. The connection tube includes a wound portion wound up by the reel body, a fixed portion that is located at a smaller distance from the inflation/deflation mechanism than the wound portion and that is fixed immovably to the case body, and a freely movable portion that is located between the wound portion and the fixed portion and that freely moves as the reel body rotates. The reel body is configured to have, on its inside, a housing that houses the freely movable portion of the connection tube and have its outer peripheral surface on which the wound portion of the connection tube is wound. In order to prevent bending of the freely movable portion of the connection tube, a first free-movement end that is a boundary between the wound portion and the freely movable portion of the connection tube is fixed to the reel body while a second free-movement end that is a boundary between the fixed portion and the freely movable portion of the connection tube is disposed at a position that is eccentric relative to a rotational center of the reel body as seen in a direction of a rotational axis of the reel body.

With this configuration, without increasing the size of the housing provided within the reel body, a large space can be ensured in which the freely movable portion of the air tube is movable, and bending of the freely movable portion of the air tube can be prevented. Therefore, the winding unit can be made compact and thus the main-unit casing of the blood pressure measuring device is not increased in size. The blood pressure measuring device can thus be provided that is compact while excellent in housing property.

Regarding the blood pressure measuring device according to the present invention, preferably a rotational direction of the reel body as the connection tube is drawn out from the winding unit is, at a position where the second free-movement end is disposed, opposite to a direction in which the connection tube at the second free-movement end extends toward the freely movable portion. Still preferably, in a state where the connection tube is wound around the reel body to a maximum extent possible, a portion that is a part of the connection tube and that extends from the second free-movement end is curved, with respect to a first straight line that overlaps the direction in which the connection tube at the second free-movement end extends toward the freely movable portion, in an opposite direction to the rotational direction of the reel body at a position that is located on an inner peripheral surface of the housing and that is opposite to the second free-movement end in the direction in which the connection tube at the second free-movement end extends toward the freely movable portion. Still preferably, supposing that the housing is divided into two regions along a second straight line that is orthogonal to the first straight line as seen in the direction of the rotational axis of the reel body and that includes the rotational center of the reel body, the second free-movement end is disposed in a region opposite to a region where the position is disposed that is located on the inner peripheral surface of the housing and that is opposite to the second free-movement end in the direction in which the connection tube at the second free-movement end extends toward the freely movable portion, or disposed on the second straight line. Still preferably, a distance between the position that is located on the inner peripheral surface of the housing and that is opposite to the second free-movement end in the direction in which the connection tube at the second free-movement end extends toward the freely movable portion, and the position of the second free-movement end is equal to or larger than a radius of the housing.

With this configuration, it is ensured that the space is large in which the freely movable portion of the air tube is movable within the small-sized housing. Thus, the winding unit can surely be downsized.

Regarding the blood pressure measuring device according to the present invention, preferably the fixed portion of the connection tube is immovably fixed to the case body by a fixed block that is immovably fixed to the case body.

With this configuration, it is easy to provide the second free-movement end at an eccentric position relative to the rotational center of the housing.

Regarding the blood pressure measuring device according to the present invention, preferably the fixed block has a bias portion, which biases with respect to a first straight line that overlaps a direction in which the connection tube at the second free-movement end extends toward the freely movable portion when the connection tube is wound around the reel body to a maximum extent possible. Another portion of the fixed block is a part of the connection tube that extends from the second free-movement end, and is biased in a direction opposite to a rotational direction of the reel body at a position that is located on an inner peripheral surface of the housing and that is opposite to the second free-movement end in the direction in which the connection tube at the second free-movement end extends toward the freely movable portion as the connection tube is drawn out.

With this configuration, in the state where the connection tube is wound up by the reel body to the maximum extent possible, there is a curved portion of the freely movable portion of the connection tube that extends from the second free-movement end, and it can be prevented that the curved portion with its shape maintained is rotated together with the reel body. Therefore, bending at this position of the connection tube can surely be prevented.

Regarding the blood pressure measuring device according to the present invention, the fixed block has a guide portion on which the freely movable portion of the connection tube is wound, in a state where the connection tube is drawn out from the winding unit.

With this configuration, as the connection tube is drawn out from the winding unit, a part of the freely movable portion of the connection tube that is wound around the fixed block is guided by the guide portion. Therefore, it can surely be prevented that the connection tube is bent at this position.

Regarding the blood pressure measuring device according to the present invention, the connection tube is formed of a plurality of tubes connected by a connector at a position where at least the first free-movement end is located.

With this configuration, the connection tube can easily be housed in the winding unit, and the connection tube can easily be fixed, at the first free-movement end, to the reel body. Therefore, workability in assembly of the winding unit is improved so that the blood pressure measuring device can be provided at low cost.

In accordance with the present invention, the winding unit can be downsized while preventing bending of the freely movable portion of the air tube within the housing provided inside the reel body. Thus, the compact blood pressure measuring device that is excellent in housing property can be provided.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

In the following, an embodiment of the present invention is described in detail with reference to the drawings. In the following embodiment, a description is given of an exemplary upper-arm blood pressure monitor which uses the oscillometric method and for which it is intended that the left upper arm is used as a site for taking a measurement.

Figure 1:
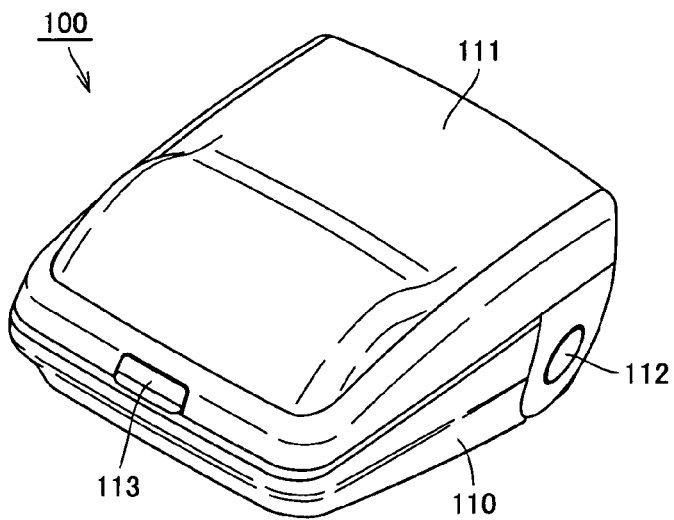
FIG. 1 is a perspective view showing an appearance of a blood pressure monitor and showing the state where an open/close cover is closed, according to an embodiment of the present invention.
Figure 2:
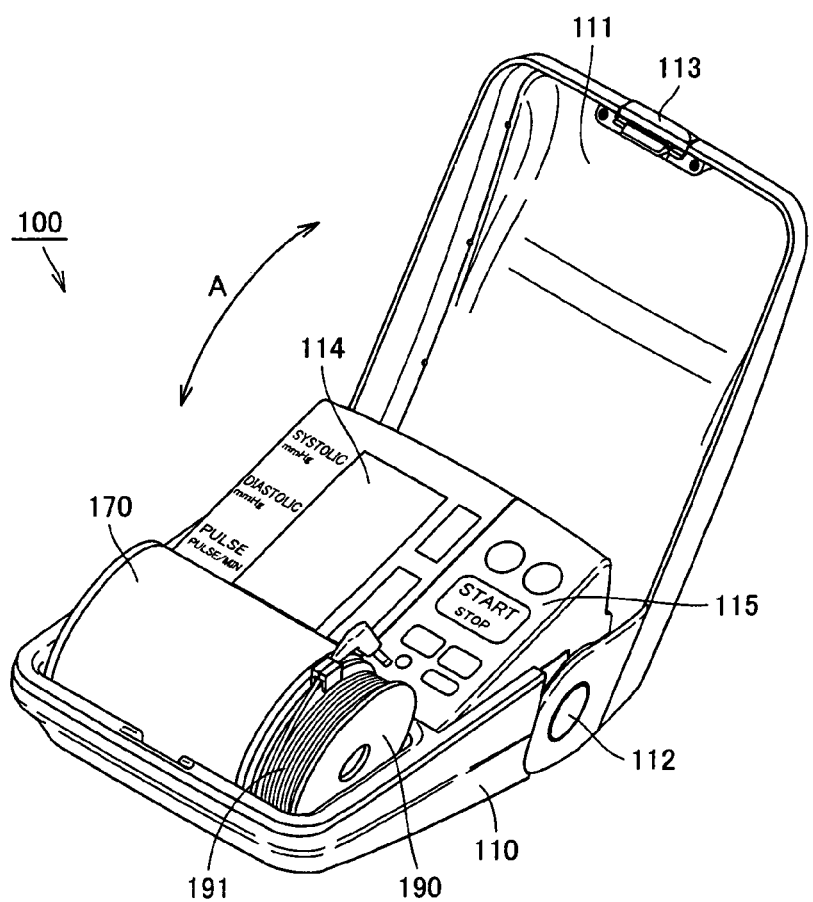
FIG. 2 is a perspective view showing an appearance of the blood pressure monitor and showing the state where the open/close cover is opened, according to the embodiment of the present invention.
Figure 3:
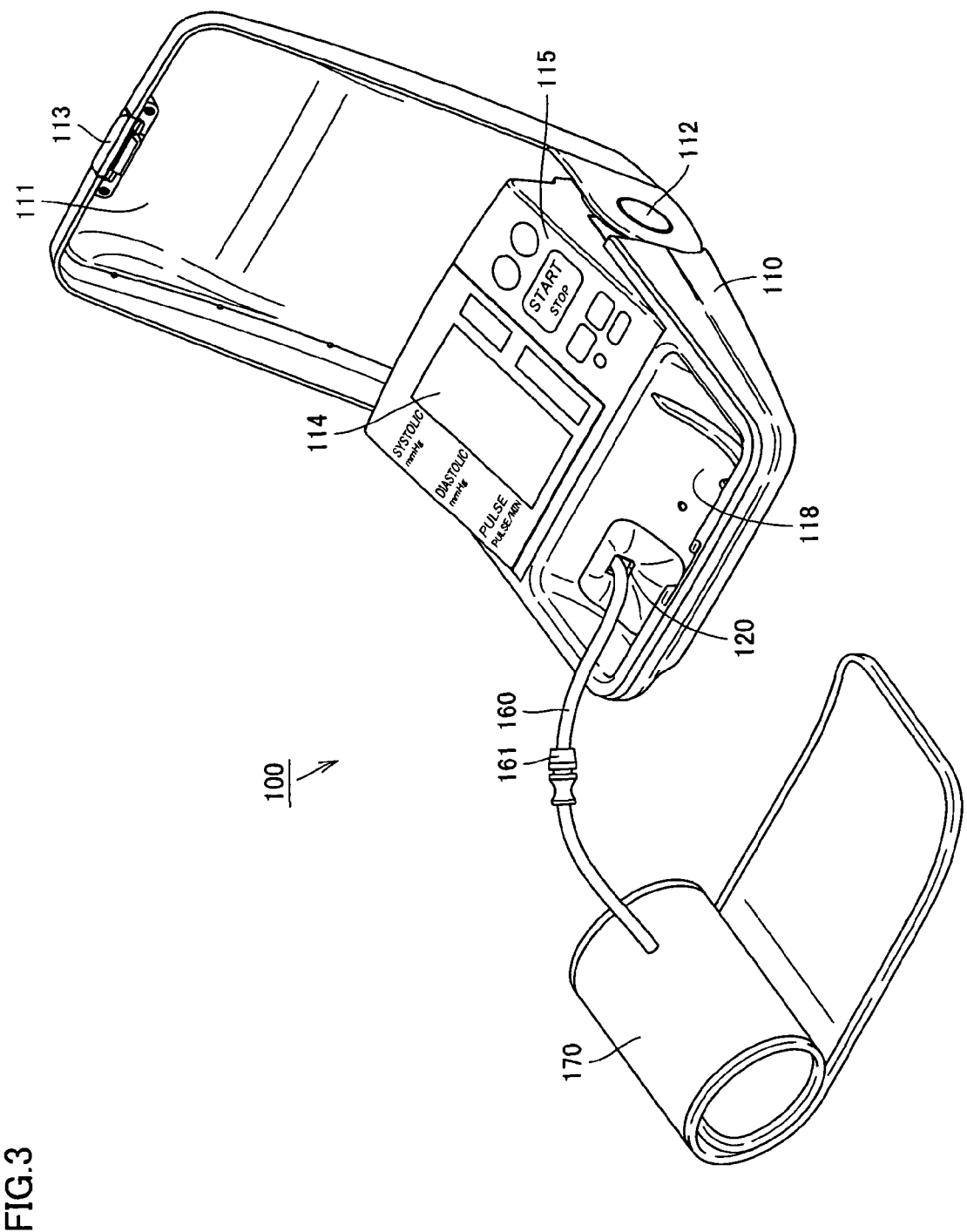
FIG. 3 is a perspective view showing an appearance of the blood pressure monitor and showing the state where the open/close cover is opened and a cuff is taken out of a main-unit casing, according to the embodiment of the present invention.

FIGS. 1 to 3 are each a perspective view showing an appearance of a blood pressure monitor according to the embodiment of the present invention. FIG. 1 is a perspective view showing the state where an open/close cover of the blood pressure monitor in the present embodiment is closed, FIG. 2 is a perspective view showing the state where the open/close cover is opened, and FIG. 3 is a perspective view showing the state where a cuff is taken out of a main-unit casing while the open/close cover is opened. First, with reference to FIGS. 1 to 3, the external structure of the blood pressure monitor in the present embodiment is described.

As shown in FIGS. 1 to 3, blood pressure monitor 100 in the present embodiment includes a main-unit casing 110 and a cuff 170 as its main components. Main-unit casing 110 has an open/close cover 111 attached in the manner that the cover in the closed state covers the upper surface of main-unit casing 110. Open/close cover 111 is pivotably coupled to main-unit casing 110 by a hinge 112 provided at a rear portion of main-unit casing 110, and pivots in the direction indicated by an arrow A in FIG. 2. For causing open/close cover 111 to change from the closed state to the opened state, an open/close button 113 provided at a front portion of open/close cover 111 is operated.

At predetermined positions of the upper surface of main-unit casing 110, such components as a display unit 114 and an operation unit 115 are provided. The display unit 114 visibly displays a measured blood pressure value and a measured pulse rate by means of numerical values and a graph for example. As display unit 114, a liquid-crystal panel for example is used. At operation unit 115, a power button and a measure/stop button for example are disposed.

In a front portion of main-unit casing 110, a cuff housing 118 is provided. Cuff housing 118 is formed by providing a depressed portion to the upper surface of main-unit casing 110. While open/close cover 111 is in the closed state, open/close cover 111 covers cuff housing 118. In blood pressure monitor 100 as shown, a housing for an AC adapter 191 is provided in parallel with cuff housing 118. In the housing of AC adapter 191, AC adapter 191 wound on a bobbin 190 is housed together with bobbin 190 while blood pressure monitor 100 is not used or a blood pressure value is measured using a DC power supply instead of the AC power supply.

As shown in FIG. 3, cuff 170 and main-unit casing 110 are connected by an air tube 160 serving as a connection tube. Air tube 160 is formed of a flexible tube and has one end drawn from an opening 120 provided in main-unit casing 110 into main-unit casing 120, and the other end connected to cuff 170. Air tube 160 has the portion drawn out from main-unit casing 110 and, at a predetermined position of that portion, a connector 161 is located that is a connecting part between a portion of the air tube that is located relatively closer to main-unit casing 110 and a portion thereof that is located relatively closer to cuff 170. Air tube 160 has one end relatively closer to cuff 170 and connected to an air bag 171 (see FIG. 4) serving as a fluid bag included in cuff 170, and air tube 160 has the other end relatively closer to main-unit casing 110 and connected via a winding unit (see FIGS. 6 to 9) provided within main-unit casing 110 to an inflation/deflation mechanism 133 (see FIG. 4) provided as well in main-unit casing 110.

Figure 4:
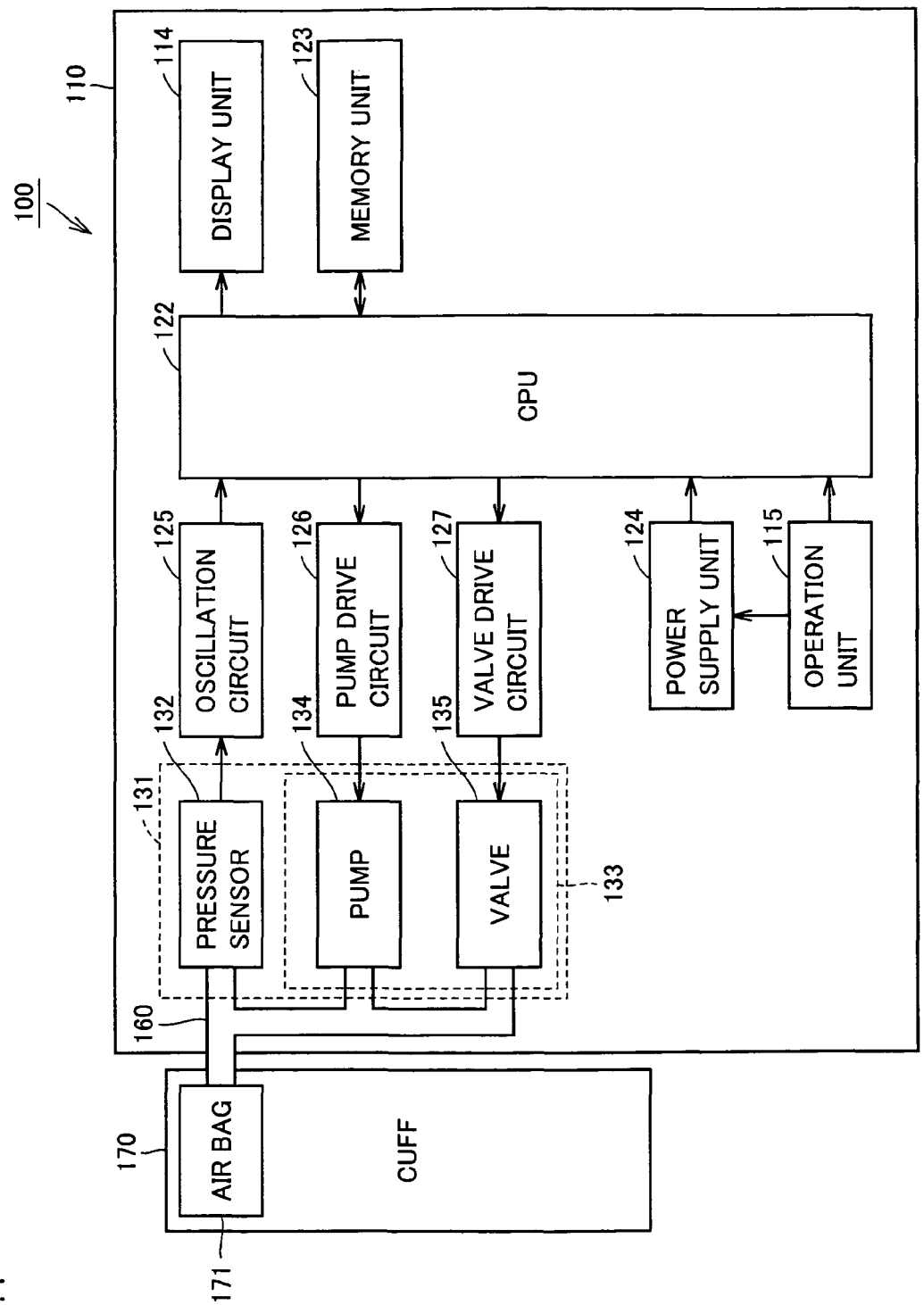
FIG. 4 is a functional block diagram showing a configuration of the blood pressure monitor according to the embodiment of the present invention.

FIG. 4 is a functional block diagram showing a configuration of the blood pressure monitor in the present embodiment. Next, with reference to FIG. 4, the configuration of main functional blocks of the blood pressure monitor in the present embodiment is described.

As shown in FIG. 4, in main-unit casing 110 of blood pressure monitor 100, an air system component for blood pressure measurement 131 is provided for supplying or discharging air through air tube 160 into or from air bag 171 contained in cuff 170. Air system component for blood pressure measurement 131 includes a pressure sensor 132 serving as a pressure detection unit detecting the pressure in air bag 171 and a pump 134 and a valve 135 that are components of inflation/deflation mechanism 133 for inflating/deflating air bag 171. Further, in main-unit casing 110, an oscillation circuit 125, a pump drive circuit 126 and a valve drive circuit 127 are provided in association with air system component for blood pressure measurement 131.

Furthermore, in main-unit casing 110, there is provided a CPU (Central Processing Unit) 122 for centralized control and monitor of the components, a memory unit 123 for storing a program for allowing CPU 122 to perform a predetermined operation as well as various information such as a measured blood pressure value, display unit 114 for displaying various information including the result of measurement of a blood pressure, operation unit 115 operated for entering various instructions for measurement, and a power supply unit 124 for supplying electric power to CPU 122 and the functional blocks each. CPU 122 also serves as a blood pressure value calculation unit for calculating a blood pressure value.

Pressure sensor 132 detects the pressure in air bag 171 (hereinafter referred to as "cuff pressure"), and outputs a signal according to the detected pressure to oscillation circuit 125. Pump 134 supplies air to air bag 171. Valve 135 opens/closes for keeping the pressure in air bag 171 or discharging the air in air bag 171. Oscillation circuit 125 outputs to CPU 122 a signal at an oscillation frequency according to the output value of pressure sensor 132. Pump drive circuit 126 controls drive of pump 134 based on a control signal provided from CPU 122. Valve drive circuit 127 controls opening/closing of valve 135 based on a control signal provided from CPU 122.

Figure 5:
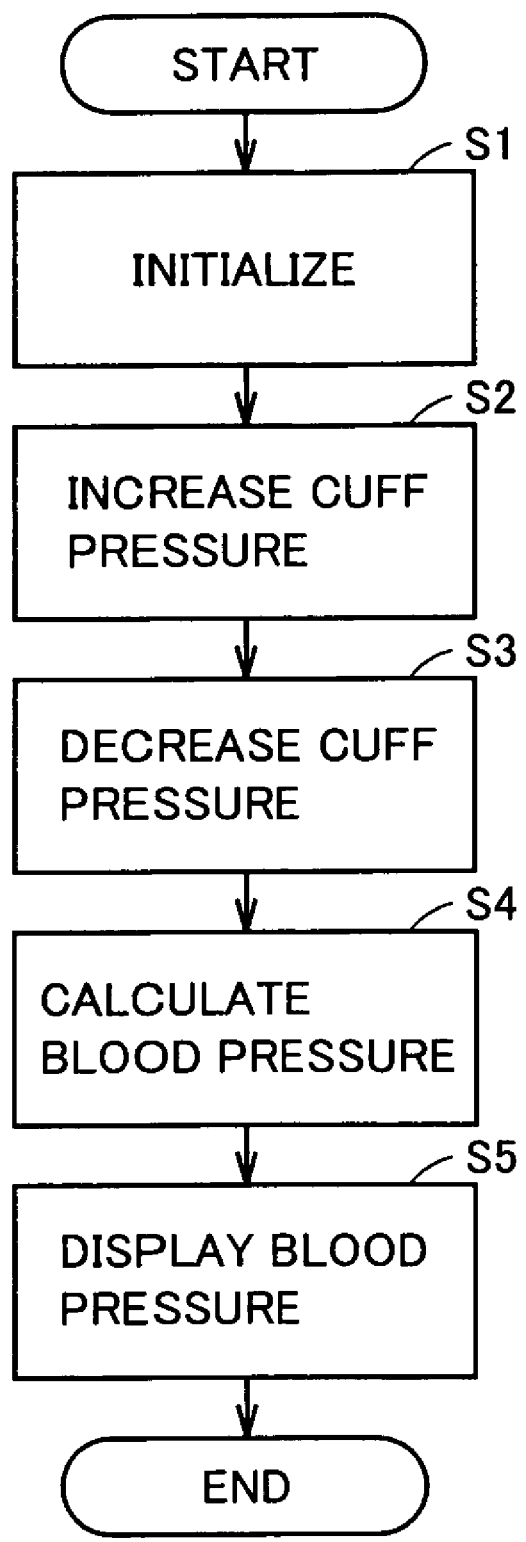
FIG. 5 is a flowchart showing a flow of a process of measuring the blood pressure by the blood pressure monitor according to the embodiment of the present invention.

FIG. 5 is a flowchart showing a flow of a process of measuring a blood pressure by the blood pressure monitor in the present embodiment. Referring now to FIG. 5, a description is given of the flow of the process of measuring a blood pressure by blood pressure monitor 100 in the present embodiment. A program in accordance with the flowchart is stored in advance in memory unit 123 as shown in FIG. 4. CPU 122 reads this program from memory unit 123 and executes the program to carry out the process of measuring a blood pressure.

As shown in FIG. 5, a user operates a button of operation unit 115 of blood pressure monitor 100 to turn on the power, and accordingly blood pressure monitor 100 is initialized (step S1). Then, when the state where a measurement can be taken is reached, CPU 122 starts driving pump 134 to gradually increase the cuff pressure of air bag 171 (step S2). In the process of gradually increasing the cuff pressure, when the cuff pressure reaches a predetermined level necessary for measuring the blood pressure, CPU 122 stops pump 134 and then gradually opens valve 135 which has been closed, so as to gradually discharge the air in air bag 171 and gradually decrease the cuff pressure (step S3). Regarding blood pressure monitor 100 in the present embodiment, the blood pressure value is measured in the process of decreasing the cuff pressure at a very low rate.

Subsequently, CPU 122 calculates the blood pressure value (systolic pressure, diastolic pressure) through the known procedure (step S4). Specifically, in the stage where the cuff pressure is gradually decreased, CPU 122 extracts pulse-wave information based on the oscillation frequency obtained from oscillation circuit 125. Then, from the extracted pulse-wave information, the blood pressure value is calculated. As the blood pressure value is calculated in step S4, the calculated blood pressure value is displayed on display unit 114 (step S5). While the above-described method of taking a measurement is based on the so-called pressure-decreased stage measurement method detecting pulse waves while the pressure of the air bag is decreased, it would clearly be seen that the so-called pressure-increased stage measurement method detecting pulse waves while the pressure of the air bag is increased may be used.

Figure 6:
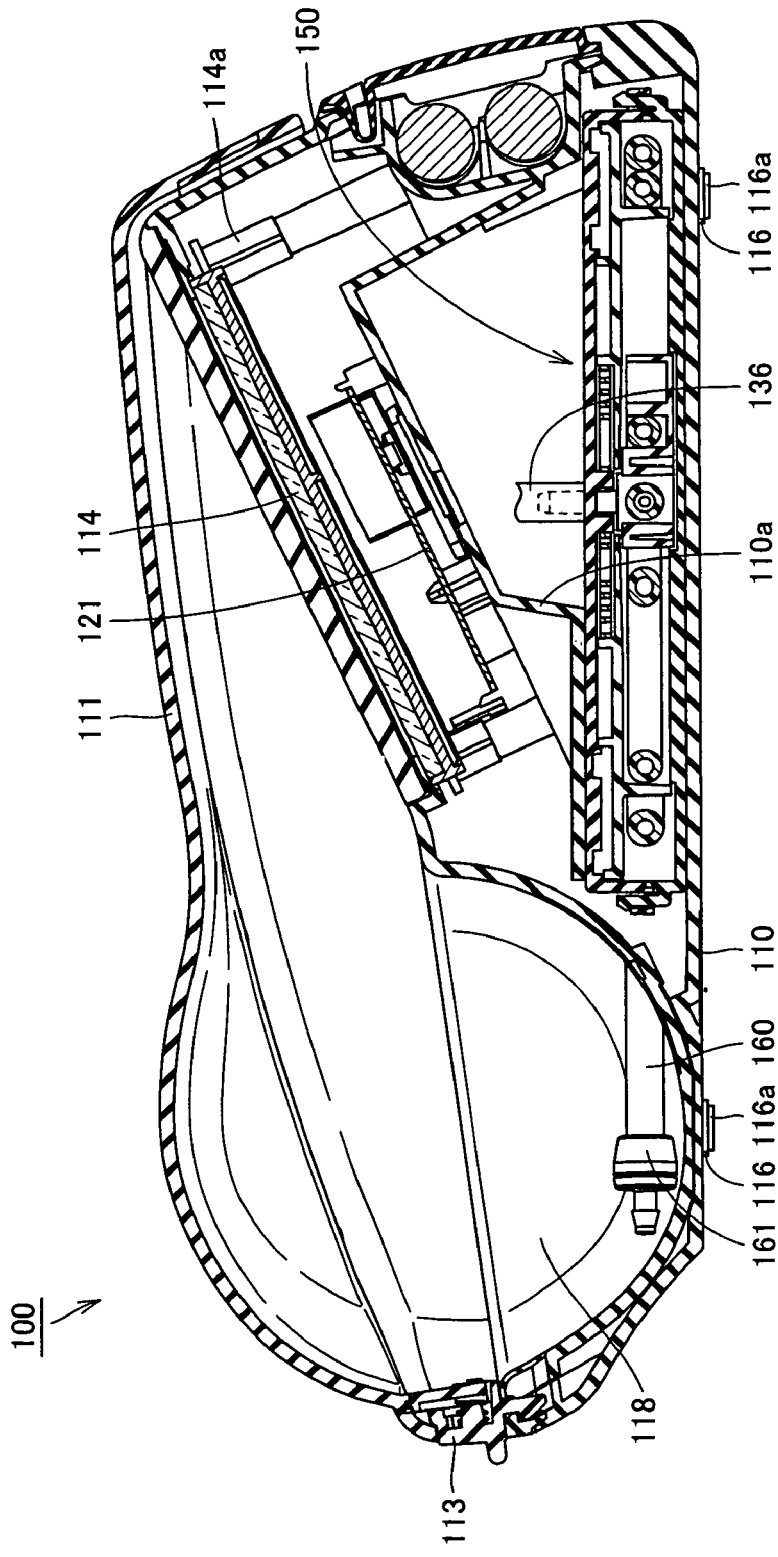
FIG. 6 is a schematic cross-sectional view showing an internal configuration of the blood pressure monitor according to the embodiment of the present invention.

FIG. 6 is a schematic cross-sectional view showing an internal structure of the blood pressure monitor in the present embodiment. In FIG. 6, the cuff, the air-tube portion connected to the cuff and the air system component for blood pressure measurement are not shown. Referring now to FIG. 6, the internal structure of the blood pressure monitor in the present embodiment is described.

As shown in FIG. 6, in blood pressure monitor 100 of the present embodiment, a partition 110*a* is provided in main-unit casing 110. Partition 110*a* divides the space within main-unit casing 110 into an upper space and a lower space. In the upper space, there is provided a circuit board 121 where such components as CPU 122, memory unit 123, oscillation circuit 125, pump drive circuit 126 and valve drive circuit 127 as described above are provided. Further, in the upper space, such a component as a display support frame 114*a* for supporting display unit 114 formed of liquid crystal display is also provided.

In the lower space, such components as a winding unit 150 allowing air tube 160 drawn out from main-unit casing 110 to be retracted into main-unit casing 110 as well as air system component for blood pressure measurement 131 (not shown) as described above are disposed. Winding unit 150 is formed of a disk-shaped assembly and is disposed horizontally in main-unit casing 110 so that the main surface of the winding unit is in parallel with the bottom surface of main-unit casing 110. Winding unit 150 is connected to air system component for blood pressure measurement 131 (not shown) by an intermediate air tube 136, and accordingly air bag 171 contained in cuff 170 is connected to air system component for blood pressure measurement 131 including inflation/deflation mechanism 133 via air tube 160 configured to be retractable into winding unit 150 and via intermediate air tube 136.

As shown in FIG. 6, at predetermined positions of the bottom surface of main-unit casing 110, a plurality of legs 116 protruding downwardly are provided. Legs 116 are components for stably mounting main-unit casing 110 of blood pressure monitor 100 on such a mount surface as table. A rubber member 116a is attached to the leading end of the legs each. Rubber member 116a is used for preventing, by friction, main-unit casing 110 from slipping to move on the mount surface while air tube 160 is drawn out from main-unit casing 110 or retracted into main-unit casing 110.

Figure 7:
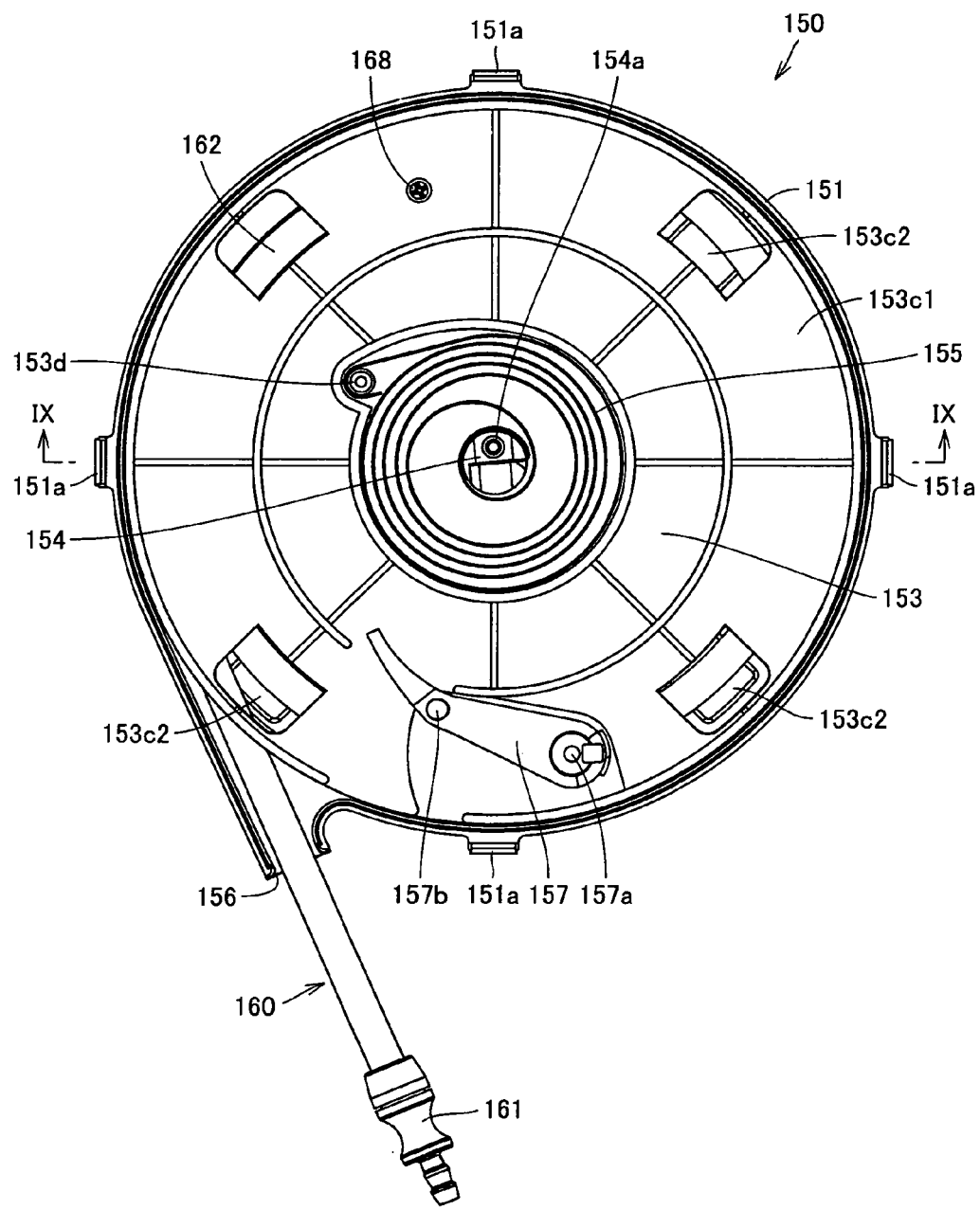
FIG. 7 is a partially-cut-away plan view of a winding unit provided to a blood pressure monitor according to the embodiment of the present invention.
Figure 8:
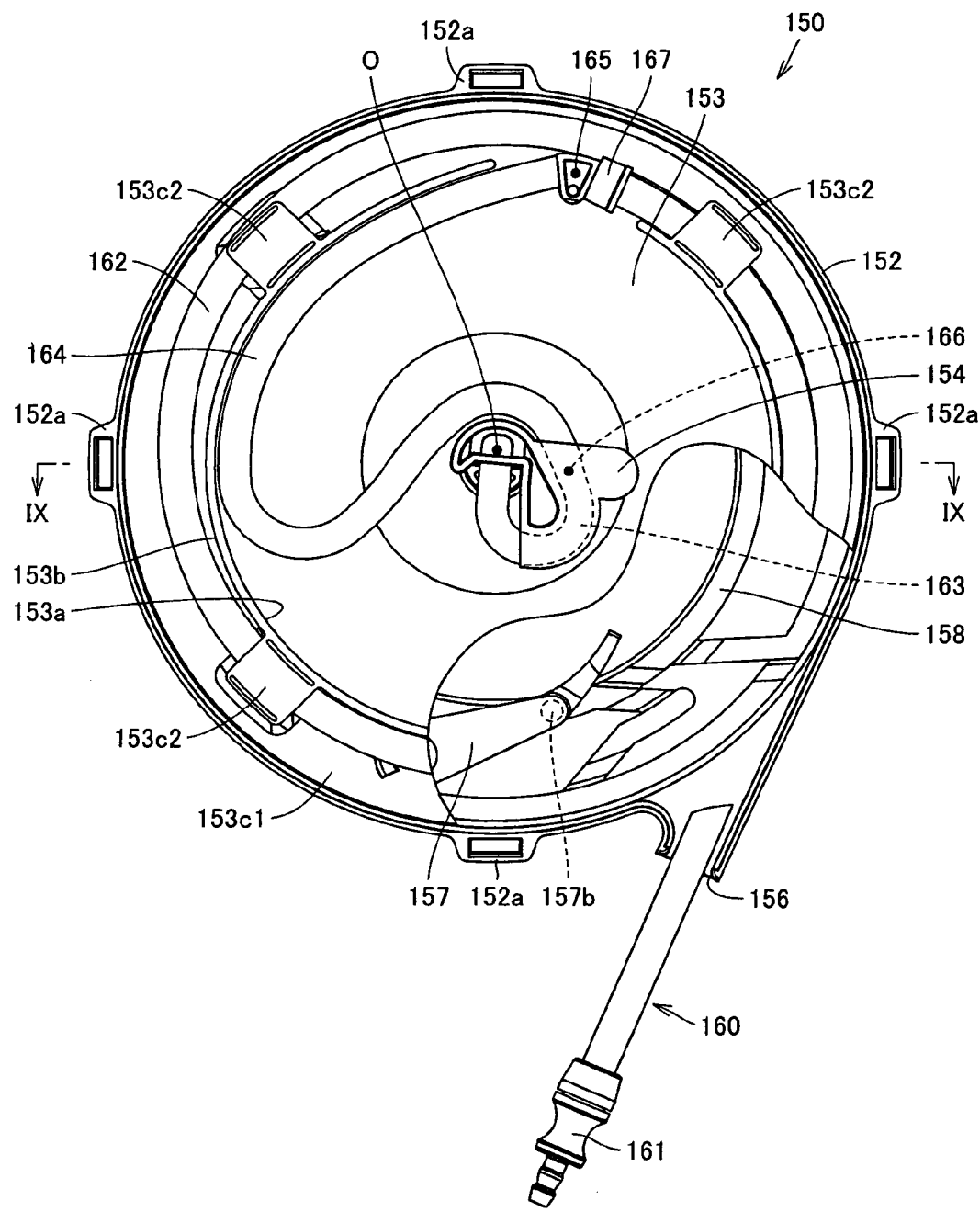
FIG. 8 is a bottom view of the winding unit provided to the blood pressure monitor according to the embodiment of the present invention.
Figure 9:
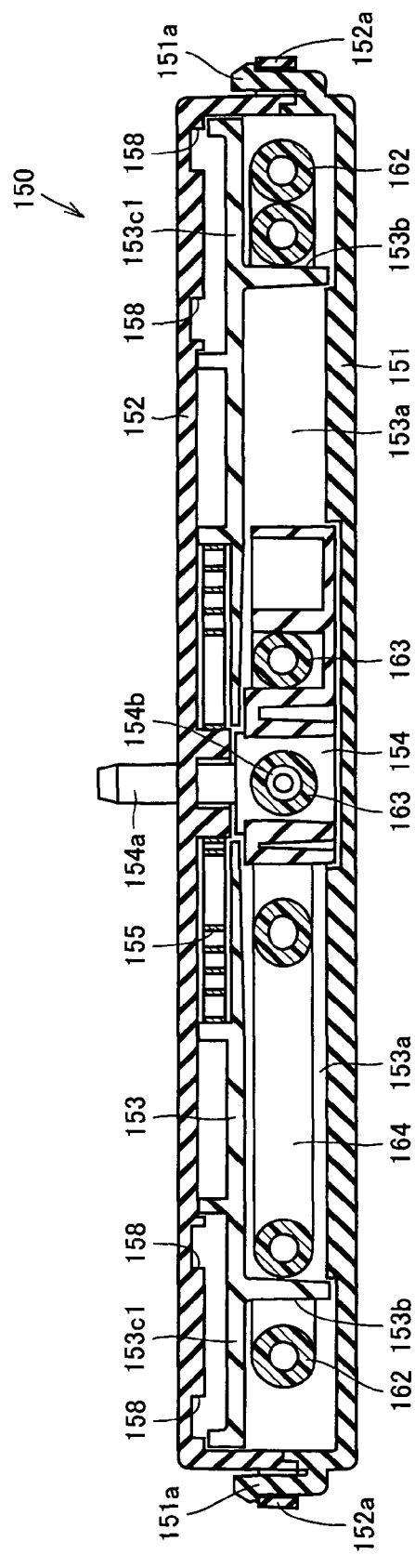
FIG. 9 is a schematic cross-sectional view of the winding unit provided to the blood pressure monitor according to the embodiment of the present invention.

FIGS. 7 to 9 each show a structure of the winding unit provided to the blood pressure monitor in the present embodiment. Of these drawings, FIG. 7 is a partially-cut-away plan view of the winding unit as seen from above and FIG. 8 is a bottom view of the winding unit as seen from below. FIG. 9 is a schematic cross-sectional view, along the line IX-IX shown in FIGS. 7 and 8, of the winding unit. In the following, with reference to FIGS. 7 to 9, the structure of the winding unit mounted in the blood pressure monitor of the present embodiment is described.

As shown in FIGS. 7 to 9, winding unit 150 provided in blood pressure monitor 100 of the present embodiment has a case body comprised of a lower case 151 and an upper case 152. Lower case 151 and upper case 152 each have a bottomed cylindrical outside shape. These lower case 151 and upper case 152 are combined to form a space in which various components are housed. Lower case 151 and upper case 152 are engaged with and secured to each other by means of a catch hook portion 151a and a catch receiving portion 152a provided on respective peripheral surfaces of these cases.

Between lower case 151 and upper case 152, the internal space of the case body is formed and, at a central position of the space, a fixed block 154 is disposed. Fixed block 154 is held between lower case 151 and upper case 152 and is fixed to the case body so that the block cannot be moved. In contrast, in the space formed between lower case 151 and upper case 152, a reel body 153 is disposed around the portion where fixed block 154 is positioned. Reel body 153 is rotatably supported by the case body. Reel body 153 has a bottomed cylindrical shape and has a housing 153a therein.

Air tube 160 is guided along a predetermined route within winding unit 150 that is comprised of the above-described case body formed of lower case 151 and upper case 152, reel body 153 and fixed block 154. Specifically, air tube 160 includes a wound portion 162, a fixed portion 163 and a freely movable portion 164 located between these wound portion 162 and fixed portion 163. Wound portion 162 is wound around an outer peripheral surface 153b of reel body 153 as described above, fixed portion 163 is fixed by fixed block 154 as described above, and freely movable portion 164 is housed in housing 153a of reel body 153 as described above. In the present embodiment, air tube 160 housed in winding unit 150 includes fixed portion 163 and freely movable portion 164 that are formed of a single tube and includes wound portion 162 formed of a tube separate from the tube forming fixed portion 163 and freely movable portion 164. These two tubes are connected via a connector 167.

Air tube 160 has a first free-movement end 165 that is the boundary between wound portion 162 and freely movable portion 164 and that is fixed to reel body 153 as well as a second free-movement end 166 that is the boundary between fixed portion 163 and freely movable portion 164 and that is fixed to fixed block 154. Specifically, connector 167 is secured to reel body 153 with a screw 168 and thereby secures first free-movement end 165 to reel body 153, while second free-movement end 165 is directly secured to fixed block 154. Further, fixed portion 163 of air tube 160 has one end connecting to freely movable portion 164 and the other end connected to fixed block 154. Wound portion 162 has one end connecting to freely movable portion 164 and the other end drawn out, from a draw-out opening 156 provided in the peripheral surface of the case body, to the outside of the case body.

Reel body 153 is provided with a flange 153c1 and a plurality of guide projections 153c2 extending outwardly from outer peripheral surface 153b of the reel body. Flange 153c1 prevents wound portion 162 of air tube 160 that is wound around outer peripheral surface 153b of reel body 153 from contacting upper case 152. Guide projections 153c2 prevent wound portion 162 of air tube 160 that is wound around outer peripheral surface 153b of reel body 153 from contacting lower case 151.

Between upper case 152 and reel body 153, a helical spring 155 serving as a member applying elasticity is provided. Helical spring 155 has one end caught and fixed on a catch portion 153d provided to reel body 153, and the other end fixed to a substantially central portion of upper case 152. Thus, reel body 153 is biased all the time in the direction in which air tube 160 is wound up.

At a predetermined position of reel body 153, a stopper 157 is pivotably attached by a pivot axis 157a. Stopper 157 has a portion facing upper case 152 and this portion is provided with a catch projection 157b. The inner surface of upper case 152 is provided with a groove 158 having a predetermined shape. Catch projection 157b is caught in groove 158 provided to upper case 152 described above, thereby forming a latch mechanism. This latch mechanism catches reel body 153 in stepwise manner in the direction in which reel body 153 is rotated, in order to keep the length of a drawn-out portion of air tube 160 in stepwise manner. This latch mechanism is available from any of well-known techniques (for example, the techniques disclosed in Japanese Patent Laying-Open Nos. 2002-226145 and 2002-274761). According to user's operation of drawing out air tube 160, the air tube is drawn out by a predetermined extent, and the drawn-out air tube may immediately be wound by the action of helical spring 155 as described above.

Figure 10A:
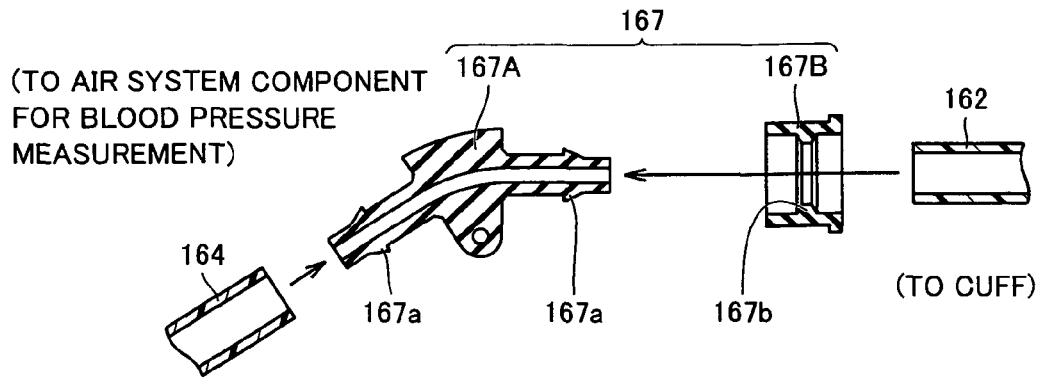
FIGS. 10A to 10C illustrate a connection structure of an air tube provided to a first free-movement end.
Figure 10B:
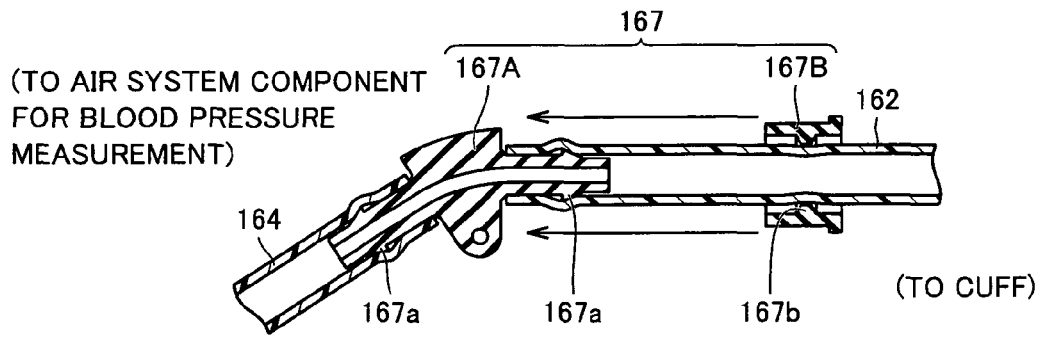
Figure 10C:
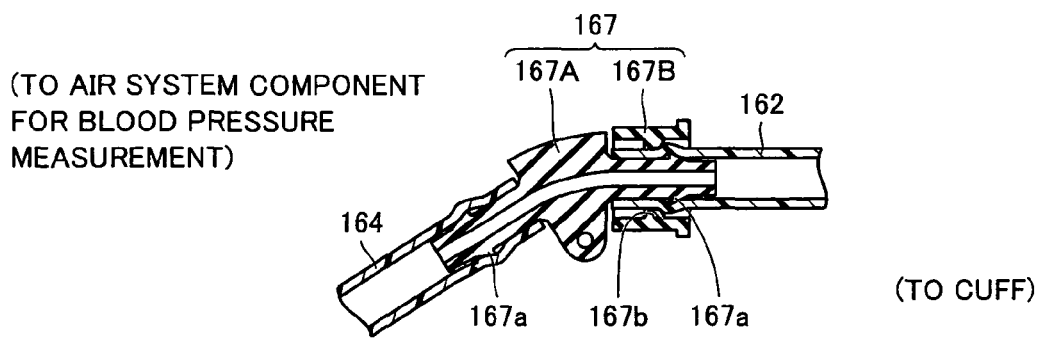

FIGS. 10A to 10C each illustrate a connection structure of the air tube provided at the first free-movement end as described above. For blood pressure monitor 100 of the present embodiment, in order to improve the workability in an assembling process of winding unit 150 and in order to easily and surely fix air tube 160 to reel body 153 and thereby form the first free-movement end 165, air tube 160 is divided at this portion into portions that are connected by connector 167. Connector 167 is comprised of two members that are a first connector member 167A and a second connector member 167B.

First connector member 167A has two opposing ends that are provided with respective connecting portions to which wound portion 162 of air tube 160 and freely movable portion 164 thereof are connected respectively. The pair of connecting portions has projections 167a that are provided respectively around the connecting portions for preventing the connected tube from being accidentally detached. The portion of the tube that is freely movable portion 164 is connected to connector 167 by means of this projection 167a only, so that this portion can be connected and disconnected relatively easily for assembly, repair, or the like. In contrast, the portion of the tube that is wound portion 162 is rarely required to be removed from connector 167. Further, if this portion is accidentally detached, winding unit 150 has to be disassembled for connecting the portion again. Therefore, this portion is more firmly secured to first connector member 167A by means of second connector member 167B. Specifically, on the inside of second connector member 167B, a projection 167b is provided for preventing accidental detachment. Between this projection 167b and projection 167a provided to first connector member 167A as described above, a part of the tube near the leading end of the tube portion that is wound portion 162 is held so as to prevent wound portion 162 from being accidentally detached from connector 167.

The tube portion that is wound portion 162 and the tube portion that is freely movable portion 164 are connected by means of connector 167 in the following way. First, as shown in FIG. 10A, second connector member 167B is fit on the tube portion that is wound portion 162. On respective connecting portions of first connector member 167A, the leading end of the tube portion that is wound portion 162 as well as the leading end of the tube portion that is freely movable portion 164 are fit. Next, as shown in FIG. 10B, second connector member 167B fit in advance on the tube that is wound portion 162 is slid to be fixed to first connector member 167A. At this time, projection 167b provided to second connector member 167B goes beyond projection 167a provided to first connector member 167A. In this way, the connection structure as shown in FIG. 10C can be obtained.

Figure 11A:
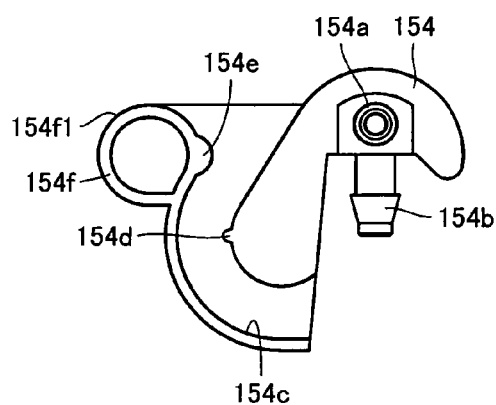
FIG. 11A is a plan view and FIG. 11B is a side view showing a shape of the fixed block.
Figure 11B:
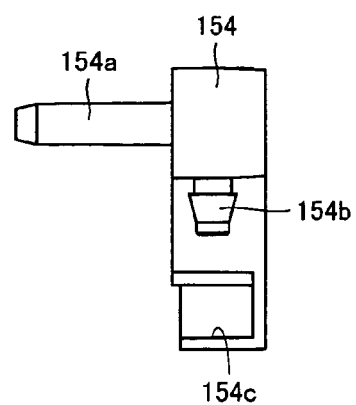
Figure 12A:
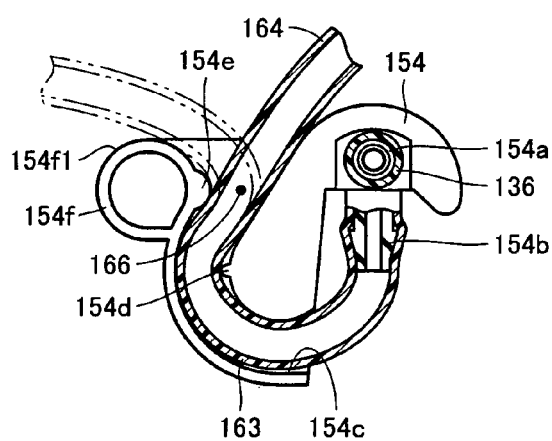
FIG. 12A is a plan view and FIG. 12B is a side view showing a state where the air tube is connected to the fixed block.
Figure 12B:
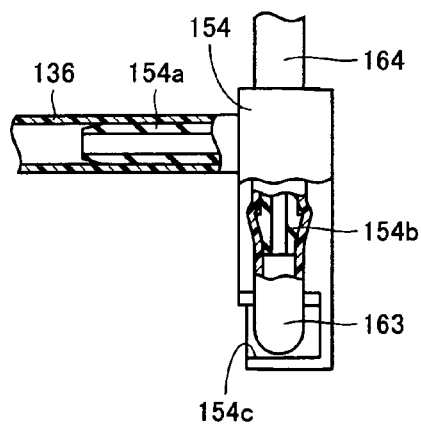

FIGS. 11A and 11B show the shape of the fixed block as described above. FIG. 11A is a plan view and FIG. 11B is a side view of the fixed block. Further, FIGS. 12A and 12B show the state in which the air tube is connected to the fixed block. FIG. 12A is a plan view and FIG. 12B is a side view showing the state in which the air tube is connected to the fixed block.

As shown in FIGS. 11A and 11B, fixed block 154 has a connecting portion 154a provided to upwardly protrude and a connecting portion 154b provided to laterally protrude. As shown in FIGS. 12A and 12B, to connecting portion 154a provided to upwardly protrude, an end of intermediate air tube 136 connected to inflation/deflation mechanism 133 is connected. To connecting portion 154b provided to laterally protrude, an end of air tube 160 routed within winding unit 150 (an end of fixed portion 163) is connected. These connecting portions 154a, 154b are communicated with each other by a communication path provided within fixed block 154. Accordingly, intermediate air tube 136 connected to fixed block 154 and air tube 160 communicate with each other.

Fixed block 154 has an air-tube-disposed path 154c that receives air tube 160. At a predetermined position of air-tube-disposed path 154c, a projection 154d is provided. This projection 154d is used to fix, within air-tube-disposed path 154c, air tube 160 which is disposed in air-tube-disposed path 154c. Thus, fixed portion 163 of air tube 160 is formed. Such a fixing structure for air tube 160 as described above is employed to form, in the vicinity of projection 154d, second free-movement end 166 that is the boundary between fixed portion 163 and freely movable portion 164 of air tube 160, as shown in FIG. 12A.

Further, at a predetermined position of air-tube-disposed path 154c, a bias portion 154e is provided to protrude from air-tube-disposed path 154c. Bias portion 154e is a component that biases, in the way as described below, a portion that is a part of air tube 160 and that extends from second free-movement end 166 toward freely movable portion 164. Specifically, with respect to a first straight line 181 (see FIG. 18 or 19) that overlaps the direction in which air tube 160 at second free-movement end 166 extends toward freely movable portion 164, the aforementioned portion of air tube 160 is biased in the direction opposite to the rotational direction (indicated by an arrow C shown in FIGS. 14 to 17) at a position 153a1 (see FIG. 18 or 19). Here, the rotational direction refers to the direction in which reel body 153 rotates as air tube 160 is drawn out, and position 153a1 refers to the position that is located on the inner peripheral surface of housing 153a and that is opposite to second free-movement end 166 in the direction in which air tube 160 at second free-movement end 166 extends toward freely movable portion 164.

At a portion adjacent to air-tube-disposed path 154c of fixed block 154, a guide portion 154f is provided. This guide portion 154f is a portion around which freely movable portion 164 of air tube 160 is wound in the state where air tube 160 is drawn out from winding unit 150, and is formed to have its outer peripheral surface 154f in the curved shape.

As winding unit 150 is provided in the above-described manner, second free-movement end 166, which is the boundary between fixed portion 163 of air tube 160 and freely movable portion 164 thereof, is disposed eccentrically with respect to rotational center O of reel body 153. Accordingly, bending (flexure) of freely movable portion 164 of air tube 160 is avoided even in the case where freely movable portion 164 of air tube 160 that is disposed to detour in housing 153a of reel body 153 so that it is freely movable in housing 153a is made long according to the length of the portion of air tube 160 that can be drawn out, in order to ensure at least a predetermined length of the portion of air tube 160 that can be drawn out of main-unit casing 110 of blood pressure monitor 100. This feature is described in detail together with behavior of air tube 160 within winding unit 150 when air tube 160 is drawn out.

FIGS. 13 to 17 illustrate behavior of the air tube within the winding unit when the air tube is drawn out from the winding unit configured as described above, showing respective states of stages at which the extent to which the tube is drawn out is gradually increased.

Figure 13:
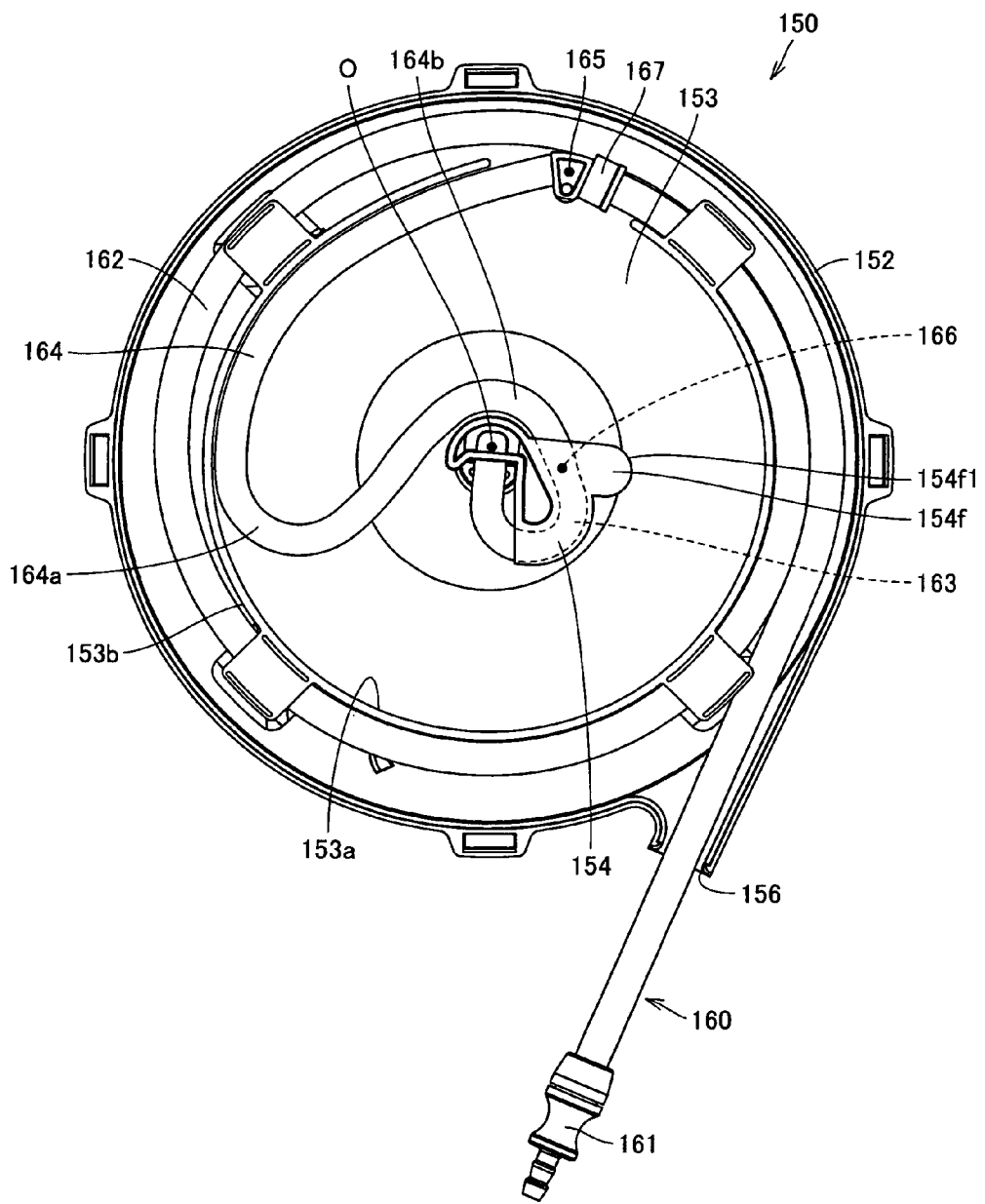
FIGS. 13 to FIG. 17 show behavior of the air tube within the winding unit when the air tube is drawn out by means of the winding unit provided to the blood pressure monitor according to the embodiment of the present invention.

As shown in FIG. 13, in the state where air tube 160 of blood pressure monitor 100 of the present embodiment is wound up around reel body 153 to the maximum extent possible, freely movable portion 164 of air tube 160 is located to greatly detour within housing 153a provided in reel body 153. This is for the following reason. Freely movable portion 164 of air tube 160 has a part that is located relatively closer to wound portion 162 of air tube 160, and this part is located to abut the inner peripheral surface of housing 153a of reel body 153. Between the part abutting the inner peripheral surface and second free-movement end 166, greatly curved portions 164a, 164b are formed at some parts of air tube 160.

Figure 14:
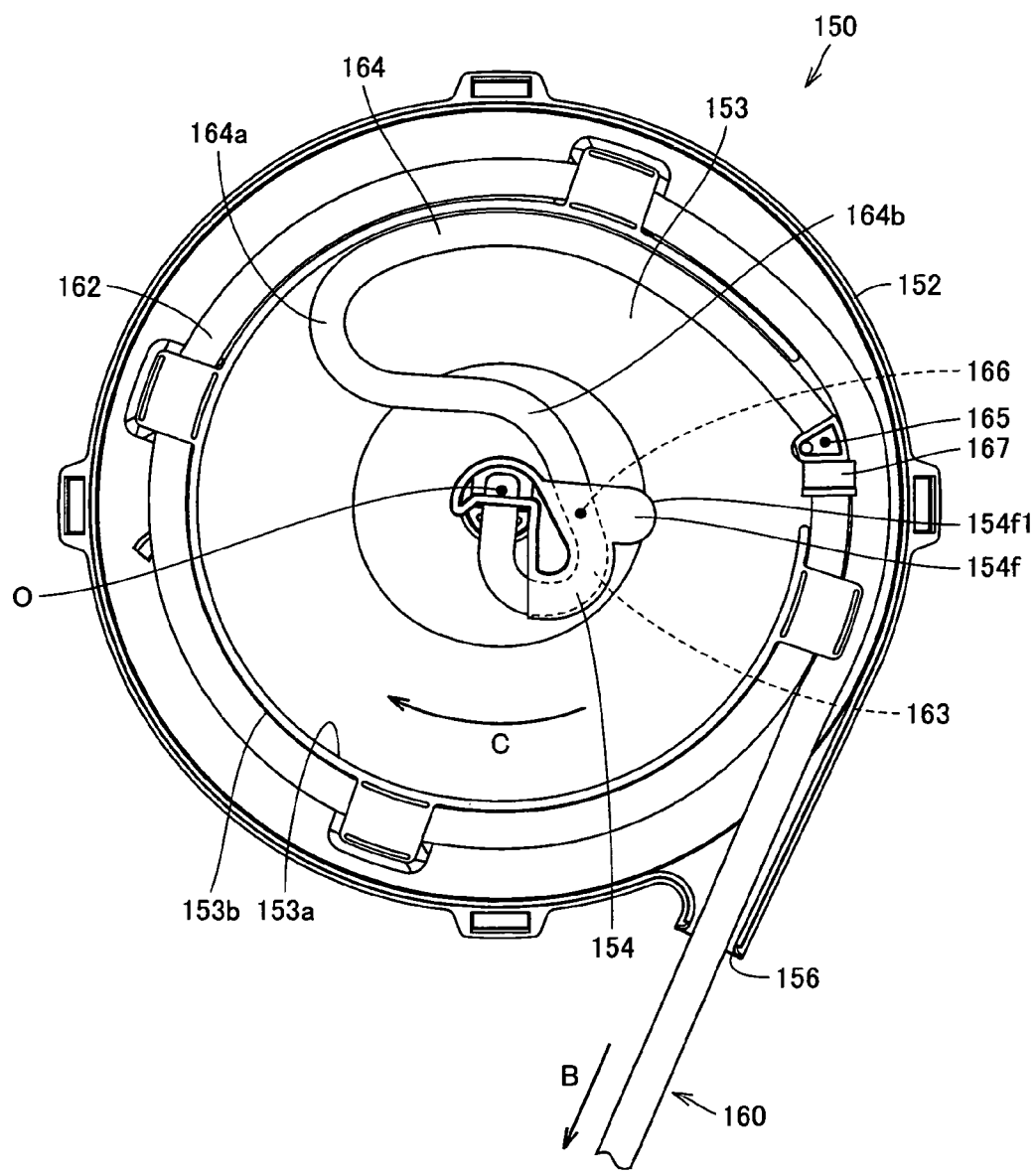

As shown in FIG. 14, air tube 160 is drawn out in the direction indicated by an arrow B as shown, and accordingly reel body 153 is rotated in the direction indicated by arrow C as shown. Since first free-movement end 165 of air tube 160 is fixed at a predetermined position of reel body 153, freely movable portion 164 is also moved within housing 153*a* as reel body 153 is rotated. At this time, since fixed portion 163 of air tube 160 is secured to fixed block 154, second free-movement end 166 does not move and stays at the position shown in FIG. 13. Accordingly, curved portion 164*a* formed at freely movable portion 164 of air tube 160 moves in the same direction as the rotational direction of reel body 153. However, air tube 160 has a portion extending from second free-movement end 166 toward freely movable portion 164 and this portion is biased in a predetermined direction by bias portion 154*e* provided to fixed block 154 as described above. Therefore, curved portion 164*b* formed at freely movable portion 164 does not move with the rotation of reel body 153 and thus stays substantially at the original position.

Figure 15:
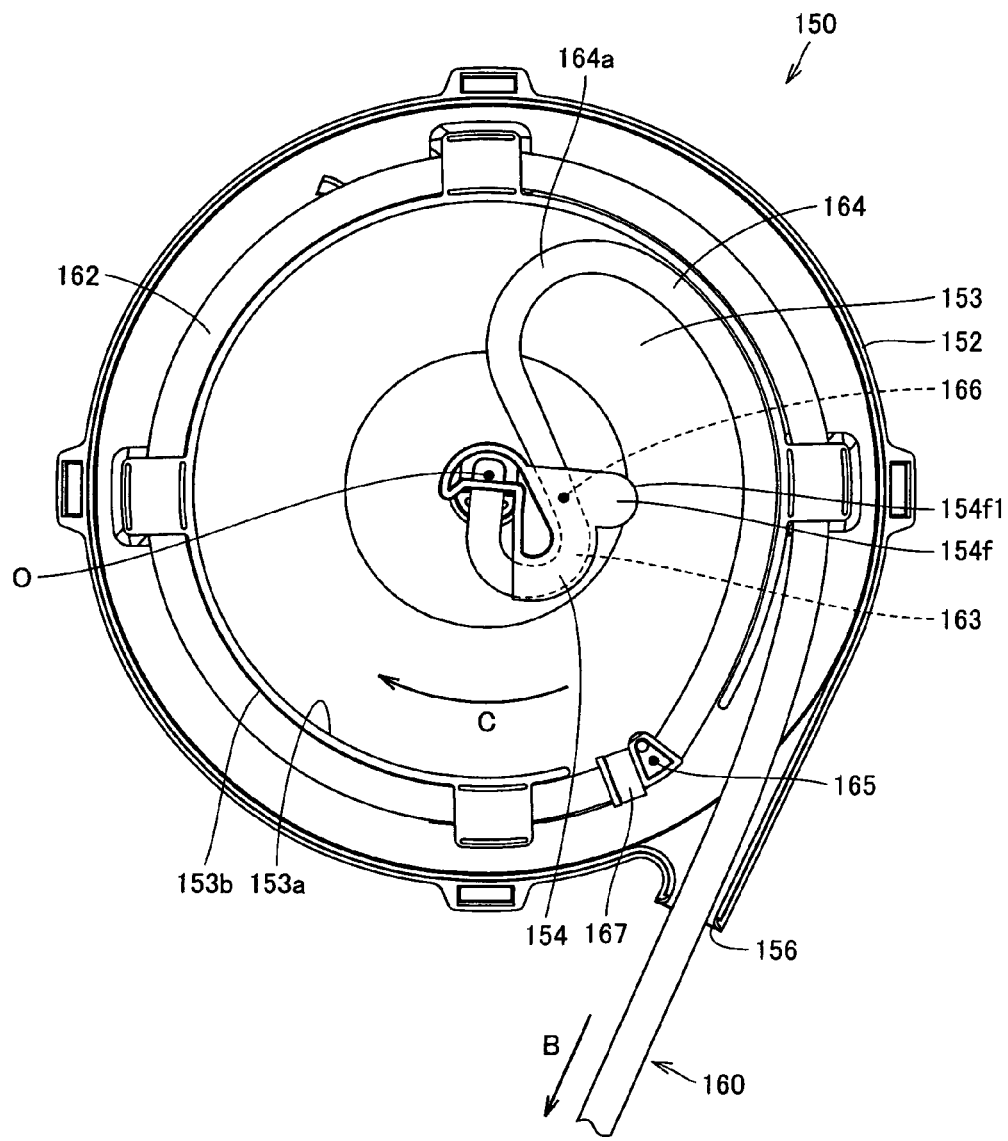

As shown in FIG. 15, when reel body 153 is rotated to a predetermined extent, movement of curved portion 164*a* as described above causes curved portion 164*b* formed relatively close to second free-movement end 166 of freely movable portion 164 to disappear. In this region where the curved portion disappears, air tube 160 extends linearly. In this case, since second free-movement end 166 of air tube 160 is located eccentrically with respect to rotational center O of reel body 153, the direction of eccentricity may be set to a predetermined direction to surely and always cause curved portion 164*b* of freely movable portion 164 to disappear. As a result, no bending is generated at curved portion 164*b* located relatively closer to second free-movement end 166 of freely movable portion 164.

Figure 16:
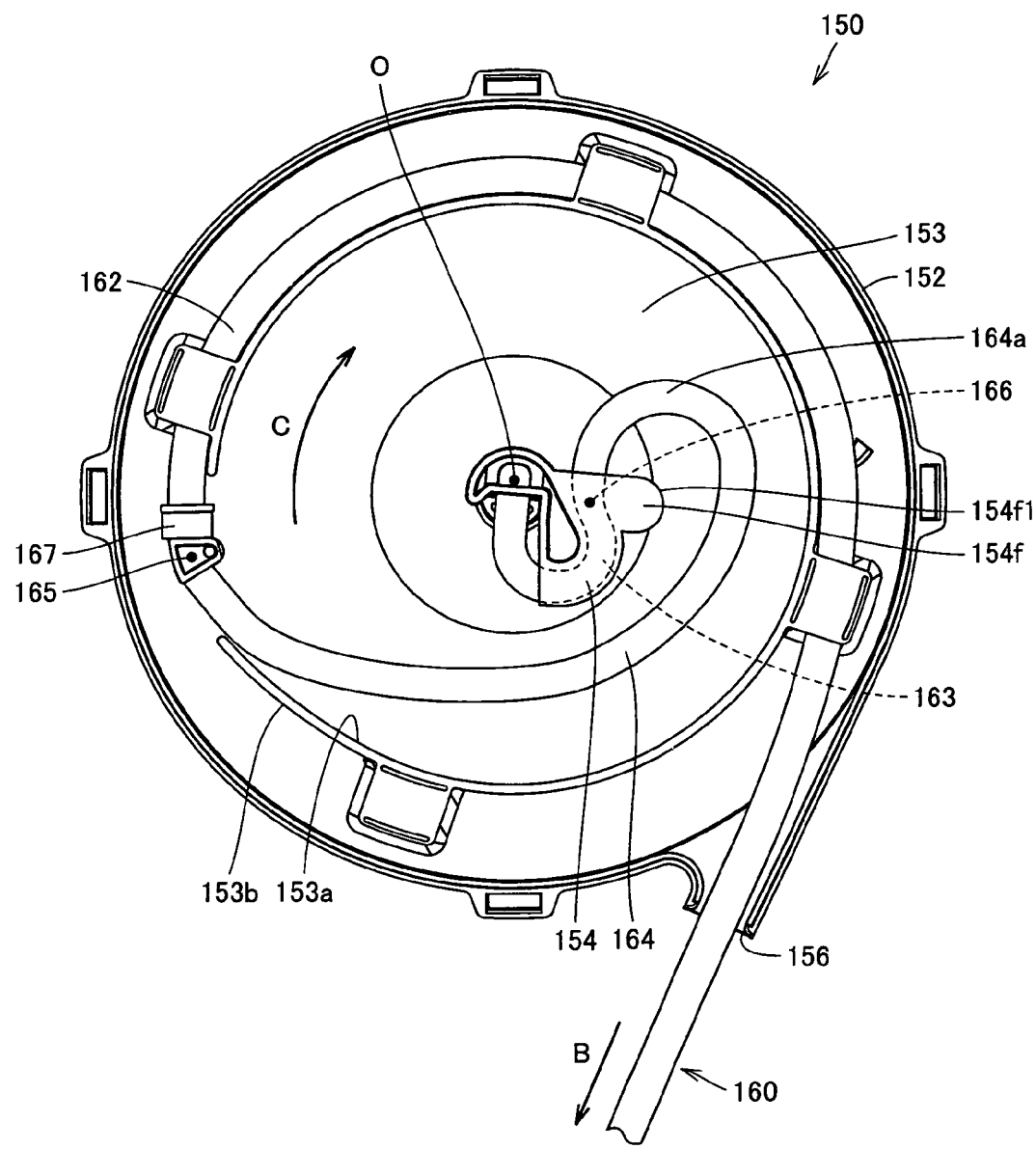
Figure 17:
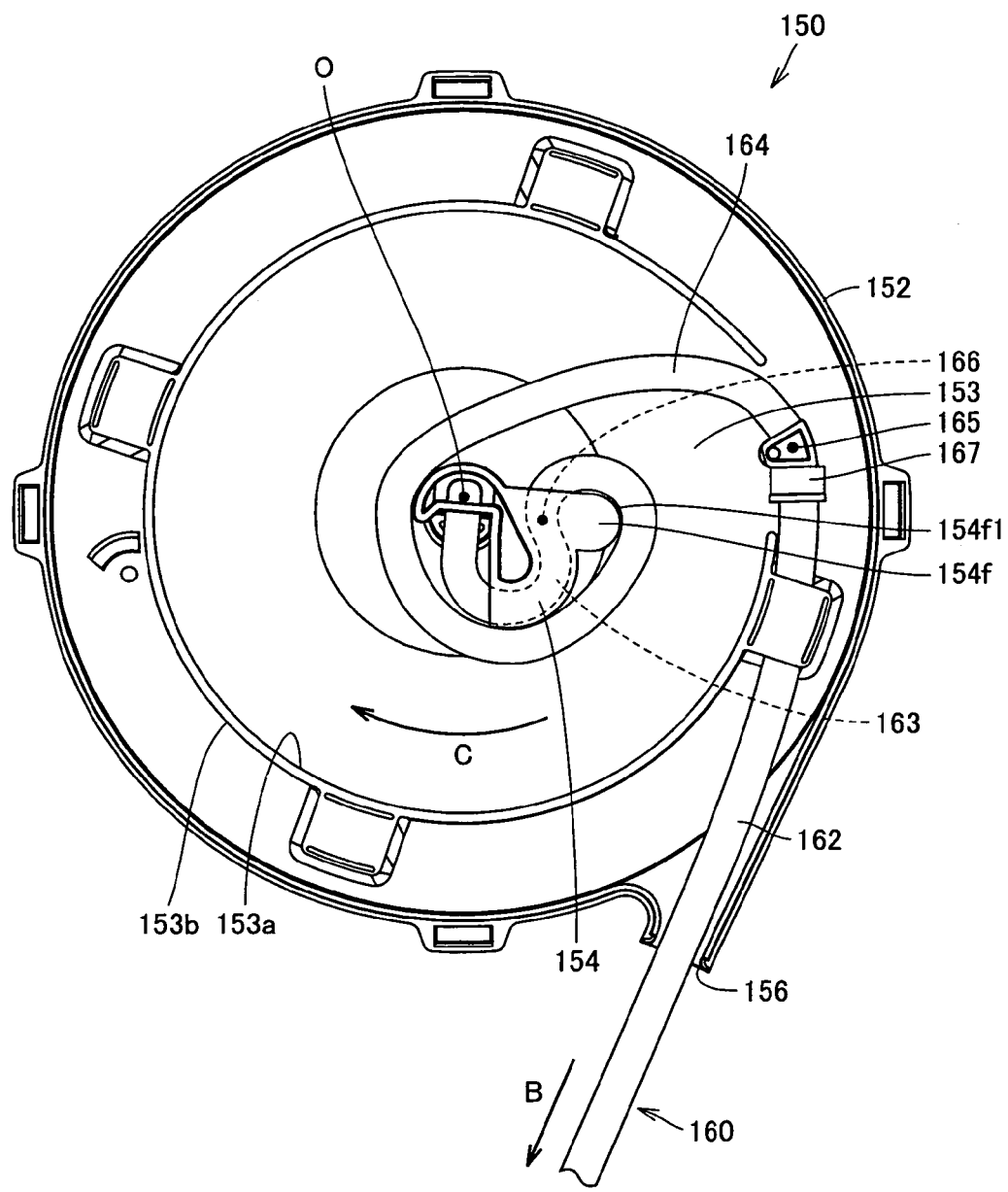

As air tube 160 is further drawn out and reel body 153 is further rotated in the direction indicated by arrow C as shown, a new curved portion is generated that curves in the opposite direction to the direction in which the now disappearing curved portion 164*b* is curved. The new curved portion is integrated with curved portion 164*a* located relatively closer to first free-movement end 165. After this, as air tube 160 is further drawn out, the state shown in FIG. 16 is generated and the state is changed to the one as shown in FIG. 17 in which air tube 160 is drawn out to the maximum extent. It is noted that a part of freely movable portion 164 of air tube 160 is wound around outer peripheral surface 154*f*1 of guide portion 154*f* provided to fixed block 154. Here, since outer peripheral surface 154*f*1 of guide portion 154*f* is formed in the curved shape as described above, no bending is generated at freely movable portion 164 of air tube 160.

As heretofore described, blood pressure monitor 100 having winding unit 150 of the present embodiment is provided to avoid increased size of housing 153*a* provided within reel body 153 while a considerably large space where freely movable portion 164 of air tube 160 is movable can be ensured. Therefore, bending of freely movable portion 164 of air tube 160 can be prevented. In this way, winding unit 150 can be downsized while increase in size of main-unit casing 110 of blood pressure monitor 100 is eliminated. Therefore, the blood pressure monitor can be made compact while being excellent in terms of housing property.

Figure 18:
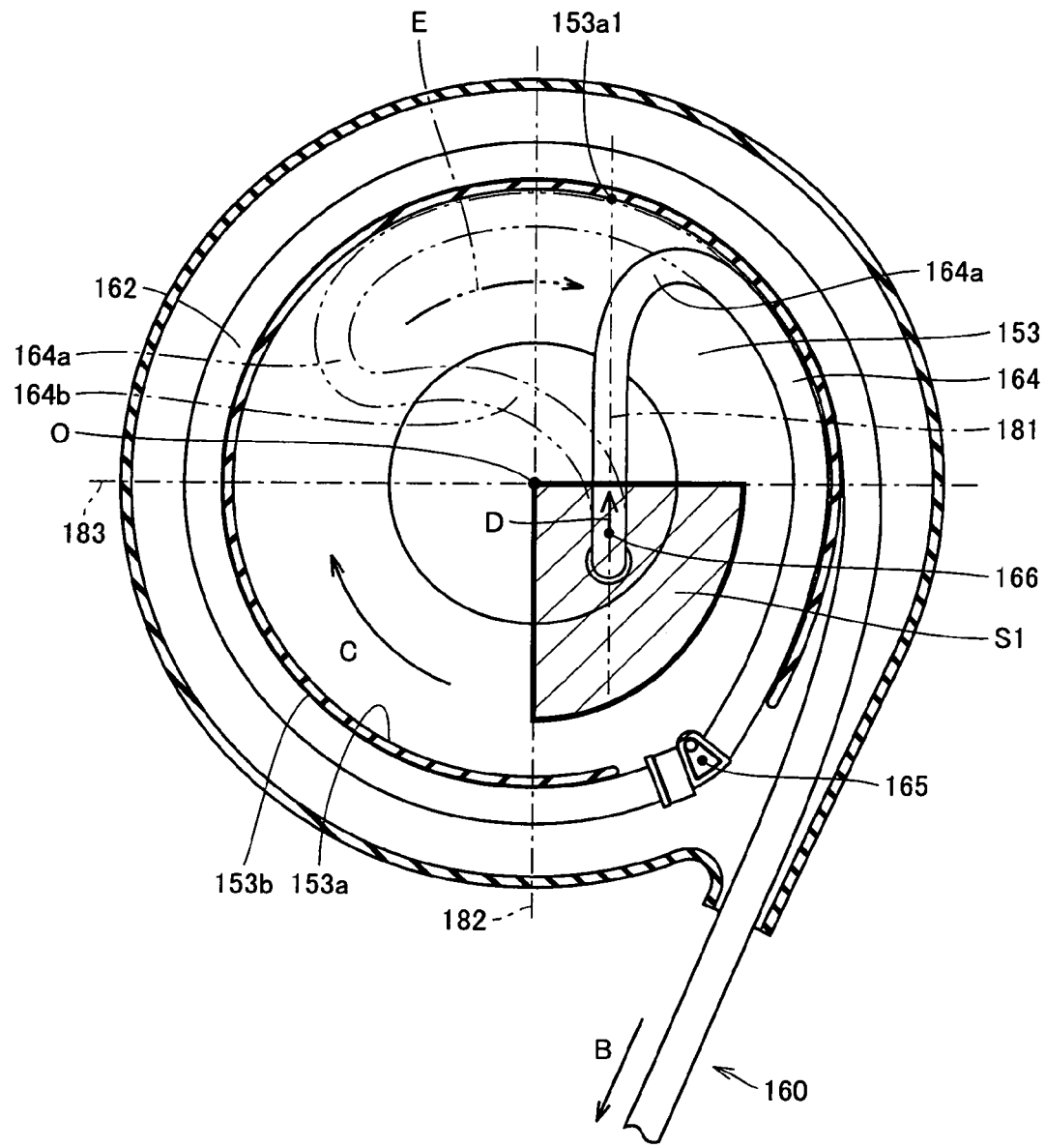
FIGS. 18 and 19 specifically illustrate a preferred direction of eccentricity of a second free-movement end.
Figure 19:
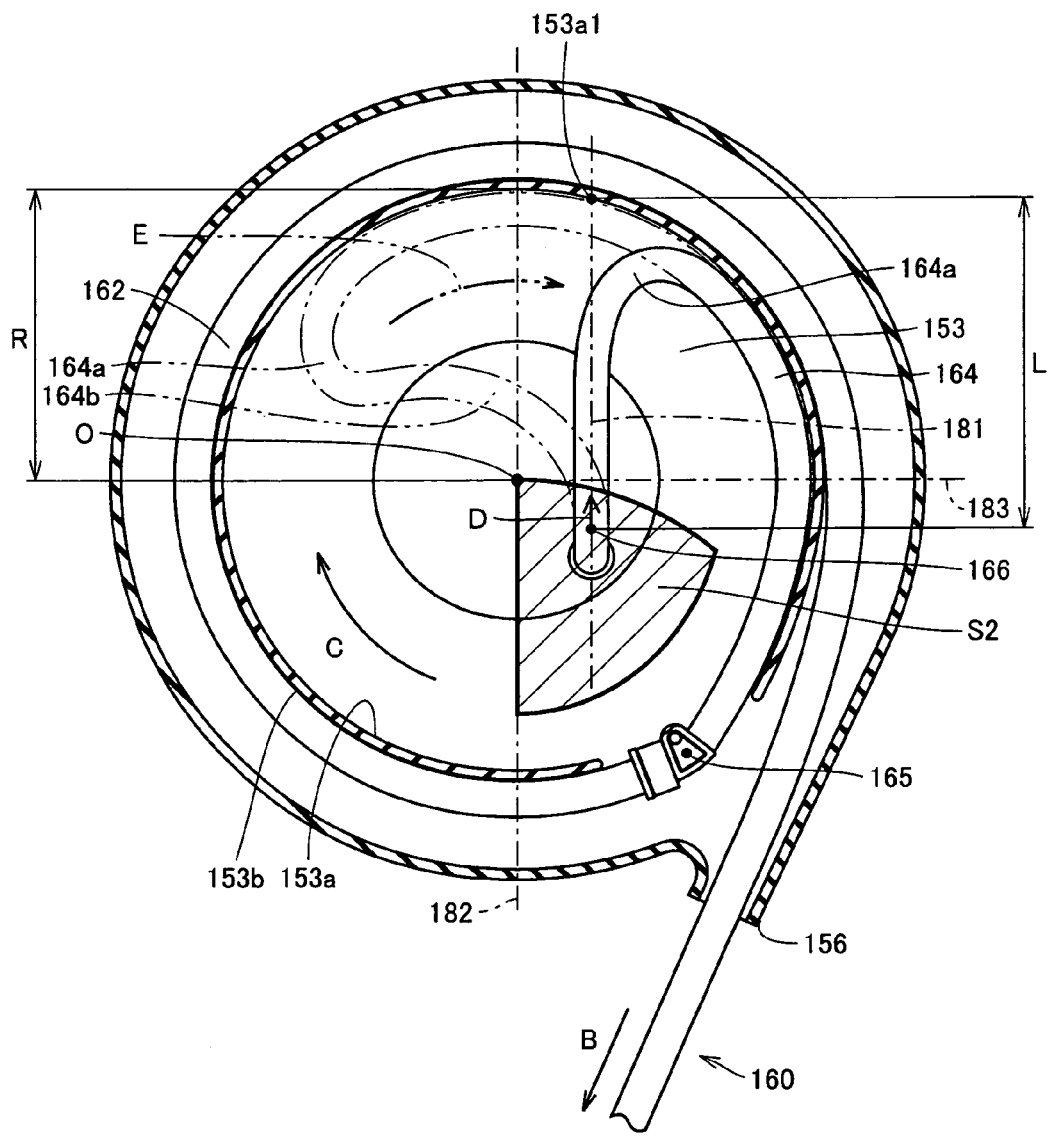
Figure 20:
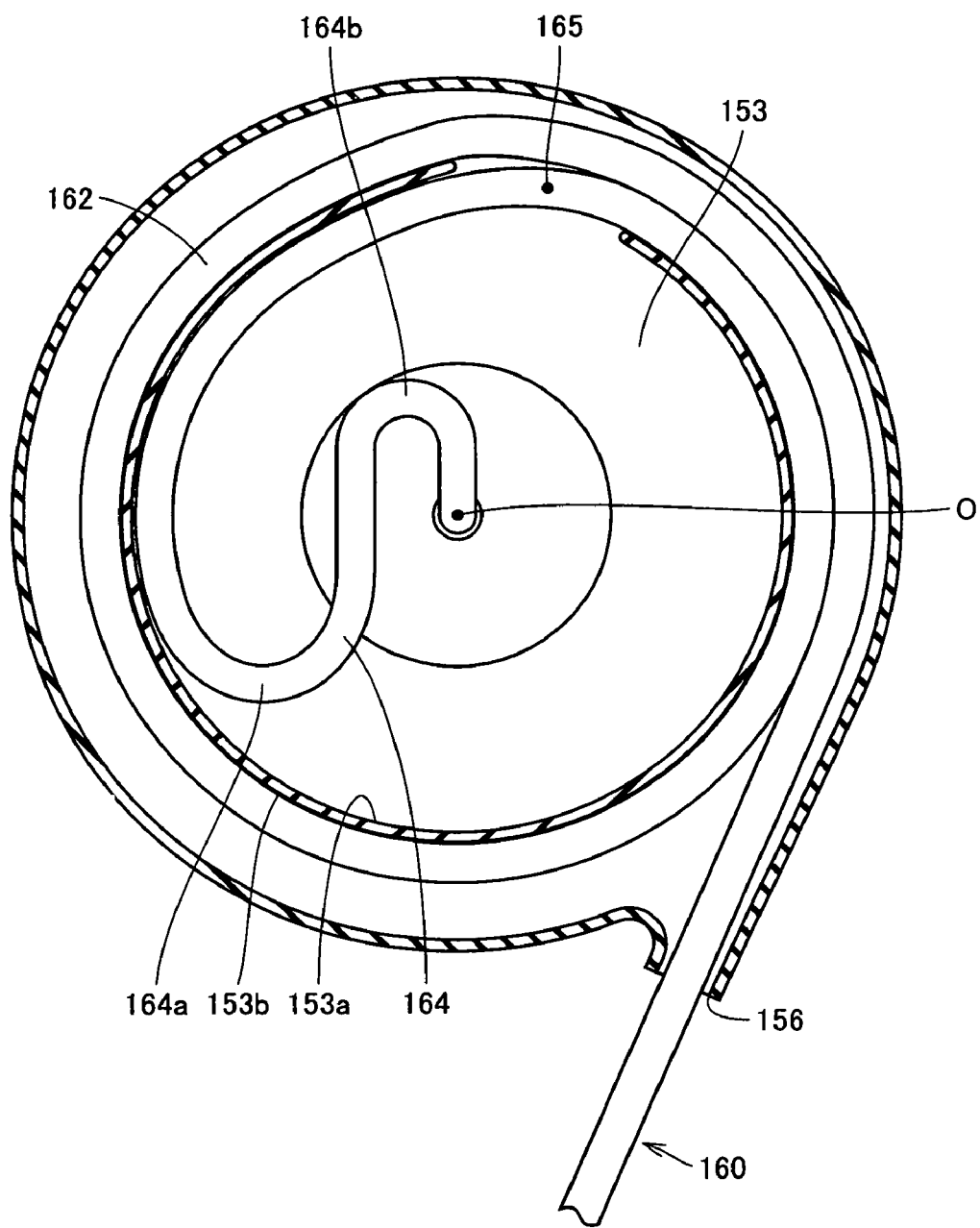
FIGS. 20 to 22 illustrate bending of the air tube that could be generated within the winding unit.
Figure 21:
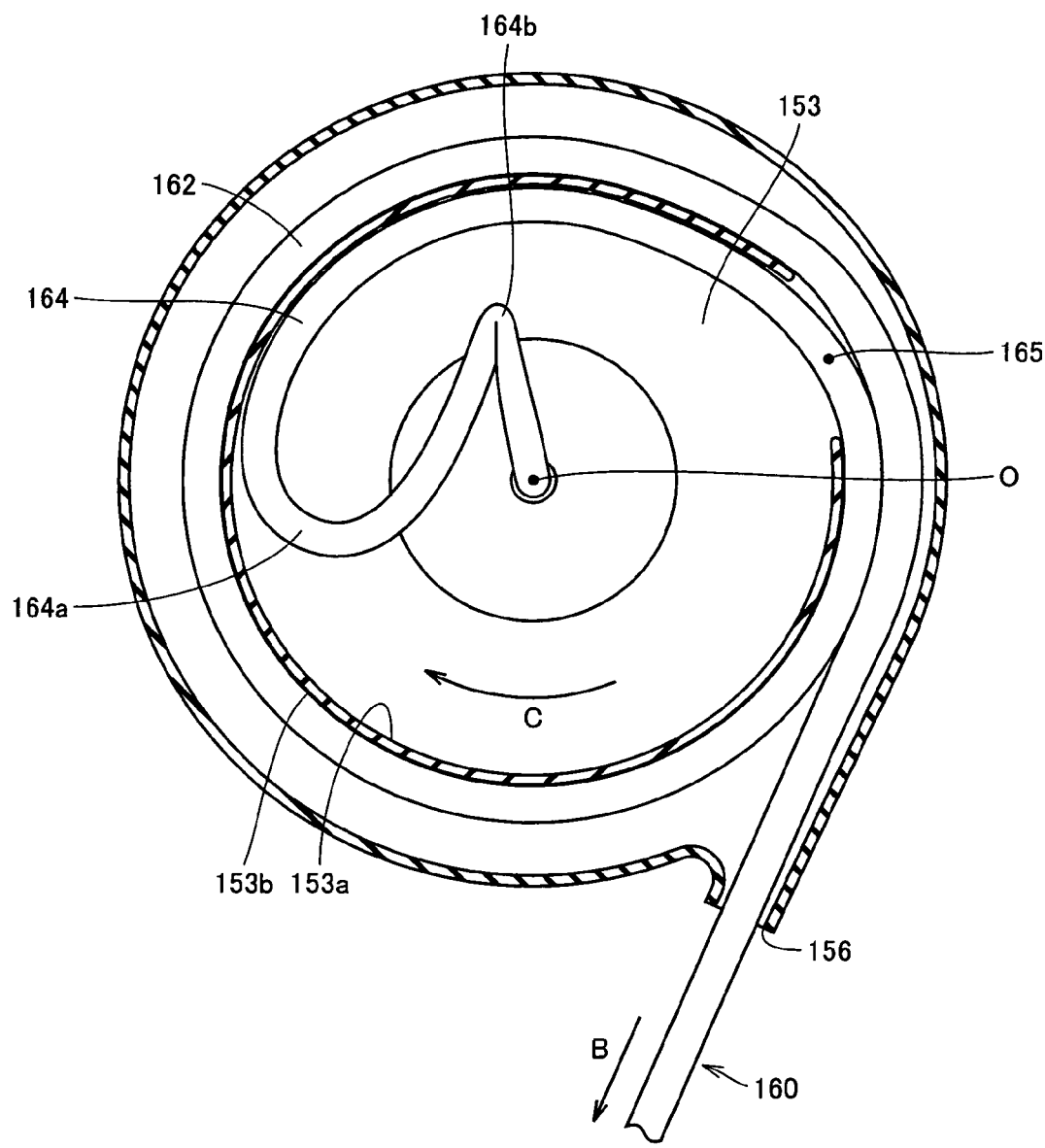
Figure 22:
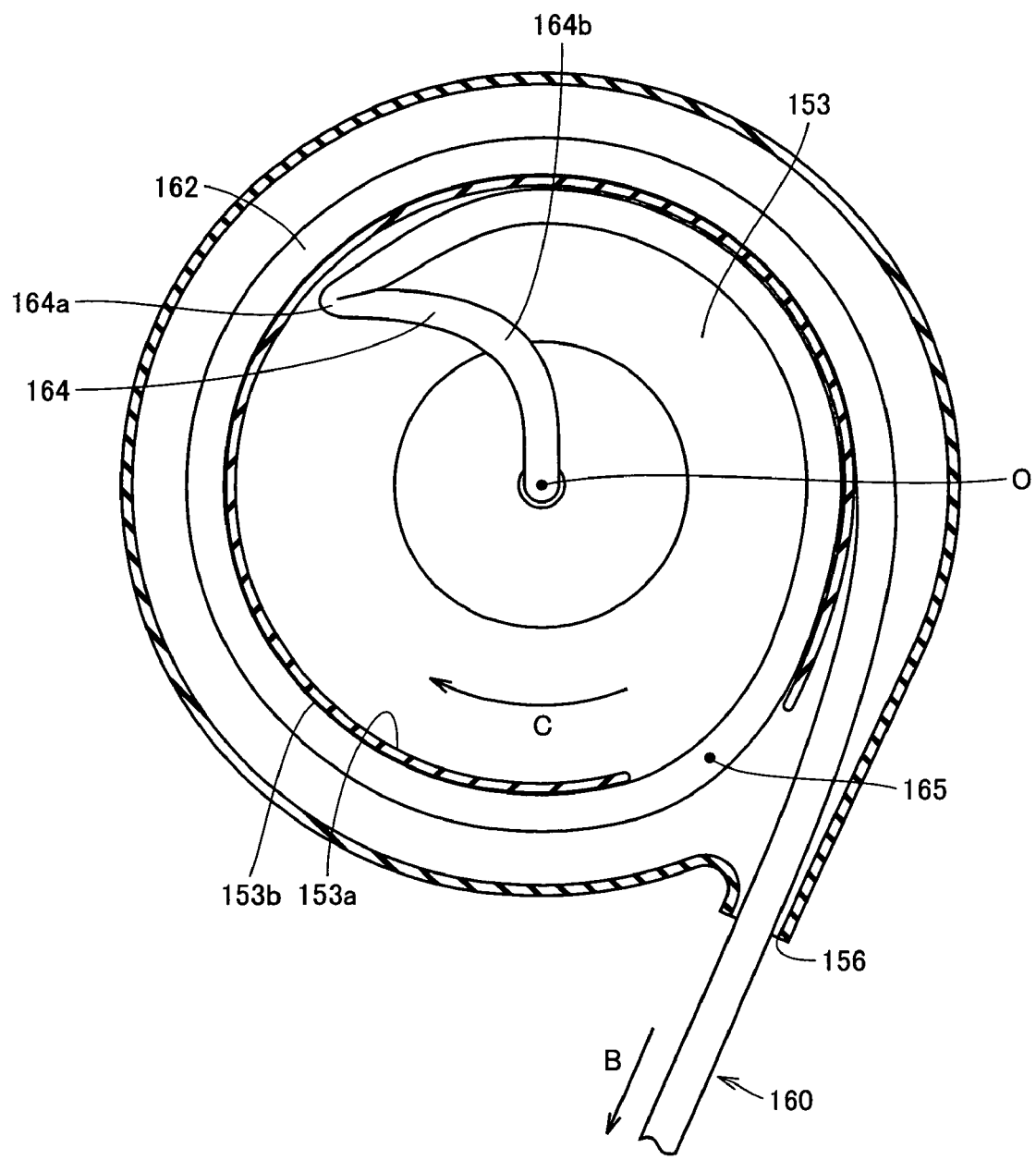

FIGS. 18 and 19 specifically illustrate a preferred direction of eccentricity of the second free-movement end. In order to ensure that a large space is provided in which freely movable portion 164 of air tube 160 can move while avoiding increase in size of housing 153*a* provided within reel body 153, it is necessary that the eccentric position of second free-movement end 166 is in a region S1 shown in FIG. 18 or a region S2 shown in FIG. 19. As long as second free-movement end 166 is disposed in the range defined by region S1, the above-described effects can be obtained for any positions of second free-movement end 166 in this region. Further, when second free-movement end 166 is disposed in the range defined by region S2, the effects can more remarkably be exhibited. For disposing second free-movement end 166 in region S1 or S2, specific conditions have to be met as described below.

First, in order to allow second free-movement end 166 to be disposed in region S1 shown in FIG. 18, the following conditions have to be satisfied. First, at the position where second free-movement end 166 is disposed, the rotational direction (indicated by arrow C as shown) of reel body 153 when air tube 160 is drawn out from winding unit 150 is opposite to the direction in which air tube 160 at second free-movement end 166 extends toward freely movable portion 164 of air tube 160 (namely the rotational direction of reel body 153 and the direction in which air tube 160 at second free-movement end 166 extends toward freely movable portion 164 are not identical but opposite to each other). Second, in the state where air tube 160 is wound around reel body 153 to the maximum extent possible, a portion that is a part of air tube 160 and that extends from second free-movement end 166 is curved, with respect to first straight line 181 that overlaps the direction (indicated by arrow D as shown) in which air tube 160 at second free-movement end 166 extends toward freely movable portion 164, in the direction opposite to the rotational direction (indicated by arrow C as shown) at position 153*a*1. Here, the rotational direction refers to the direction in which reel body 153 rotates when air tube 160 is drawn out, and position 153*a*1 refers to the position that is located on the inner peripheral surface of housing 153*a* and that is opposite to second free-movement end 166 in the direction (indicated by arrow D as shown) in which air tube 160 at second free-movement end 166 extends toward freely movable portion 164. Third, supposing that housing 153*a* is divided into two regions along a second straight line 183 that is orthogonal to first straight line 181 as seen in the direction of the rotational axis of reel body 153 and that includes rotational center O of reel body 153, second free-movement end 166 is disposed in the region opposite to the region in which position 153*a*1 on the inner peripheral surface of housing 153*a* is located, position 153*a*1 being opposite to second free-movement end 166 in the direction (indicated by arrow D as shown) in which air tube 160 at second free-movement end 166 extends toward freely movable portion 164, or disposed on second straight line 183. It is noted that a straight line 182 shown in the drawings is a straight line that is parallel to first straight line 181 as seen in the direction of the rotational axis of reel body 153 and that includes rotational center O of reel body 153. Thus, region S1 corresponds to one of the four regions into which the housing is divided along the above-described second straight line 183 and this straight line 182.

With the configuration as described above, second free-movement end 166 is disposed in region S1. Accordingly, a sufficient space is ensured in which curved portion 164*a* of freely movable portion 164 that is located relatively closer to first free-movement end 165 moves, in the direction indicated by an arrow E as shown, as reel body 153 rotates. Therefore, in this region, bending of air tube 160 is not generated. Further, curved portion 164*b* which is generated at freely movable portion 164 as reel body 153 rotates does not move and disappears at the original position. Therefore, in this region, bending of air tube 160 does not occur. In this way, it can surely be prevented that the supply of air is hindered or that the air tube is broken.

Further, in order to allow second free-movement end 166 to be disposed in region S2 shown in FIG. 19, in addition to the conditions as described above, the following condition has to be satisfied. In the state where air tube 160 is wound around reel body 153 to the maximum extent possible, a distance L between the position of second free-movement end 166 and position 153a1 on the inner peripheral surface of housing 153a that is opposite to second free-movement end 166 in the direction (indicated by arrow D as shown) in which air tube 160 at second free-movement end extends toward freely movable portion 164 is equal to or larger than a radius R of housing 153a. With this configuration, second free-movement end 166 is disposed in region S2. Accordingly, a larger space is ensured that is enough for movement of curved portion 164a that is located relatively closer to first free-movement end 165 of freely movable portion 164 and that moves in the direction indicated by arrow E in the drawing as reel body 153 rotates.

In connection with the embodiment above, the oscillometric blood pressure monitor is described as an example. However, it would naturally be understood that the present invention is also applicable to a blood pressure monitor using the Korotkoff method. In this case, a signal line provided to connect the main-unit casing and the cuff may be integrated with the air tube into a composite line or these signal line and air tube may separately be provided.

Further, in connection with the embodiment described above, it is illustrated that the latch mechanism is provided to the winding unit that fixes the rotation of the reel body in stepwise manner. Alternatively, frictional force may be exerted on the air tube to fix the air tube to allow the extent to which the air tube is drawn out to be an arbitrary extent.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood pressure measuring device comprising:
   a cuff having an inflatable/deflatable fluid bag;
   a main-unit casing in which an inflation/deflation mechanism inflating/deflating said fluid bag is disposed;
   a flexible connection tube connecting said fluid bag and said inflation/deflation mechanism; and
   a winding unit capable of retracting said connection tube that is drawn out from said main-unit casing into said main-unit casing, wherein
   said winding unit includes a case body immovably fixed to said main-unit casing, a reel body rotatably supported by said case body, and an elasticity application portion applying elasticity to said reel body in a direction in which said connection tube is wound,
   said connection tube includes a wound portion wound up by said reel body, a fixed portion that is located at a smaller distance from said inflation/deflation mechanism than said wound portion and that is fixed immovably to said case body, and a freely movable portion that is located between said wound portion and said fixed portion and that freely moves as said reel body rotates,
   said reel body is configured to have, on its inside, a housing that houses said freely movable portion of said connection tube and have its outer peripheral surface on which said wound portion of said connection tube is wound, and
   in order to prevent bending of said freely movable portion of said connection tube, a first free-movement end that is a boundary between said wound portion and said freely movable portion of said connection tube is fixed to said reel body while a second free-movement end that is a boundary between said fixed portion and said freely movable portion of said connection tube is disposed at a position that is eccentric relative to a rotational center (O) of said reel body as seen in a direction of a rotational axis of said reel body,
   wherein a distance between the position that is located on the inner peripheral surface of said housing and that is opposite to said second free-movement end in the direction (D) in which said connection tube at said second free-movement end extends toward said freely movable portion, and the position of said second free-movement end is equal to or larger than a radius (R) of said housing.

2. The blood pressure measuring device according to claim 1, wherein
   said fixed portion of said connection tube is immovably fixed to said case body by a fixed block that is immovably fixed to said case body.

3. The blood pressure measuring device according to claim 2, wherein
   said fixed block has a bias portion biasing, in a state where said connection tube is wound around said reel body to a maximum extent possible, with respect to a first straight line that overlaps a direction in which said connection tube at said second free-movement end extends toward said freely movable portion, a portion that is a part of said connection tube and that extends from said second free-movement end, and said portion is biased in a direction opposite to a rotational direction (C) of said reel body as said connection tube is drawn out, at a position that is located on an inner peripheral surface of said housing and that is opposite to said second free-movement end in the direction (D) in which said connection tube at said second free-movement end extends toward said freely movable portion.

4. The blood pressure measuring device according to claim 2, wherein
   said fixed block has a guide portion on which said freely movable portion of said connection tube is wound, in a state where said connection tube is drawn out from said winding unit.

5. The blood pressure measuring device according to claim 1, wherein
   said connection tube is formed of a plurality of tubes connected by a connector at a position where at least said first free-movement end is located.

* * * * *